(12) United States Patent
Cheng et al.

(10) Patent No.: US 10,611,799 B2
(45) Date of Patent: Apr. 7, 2020

(54) ANTI-ENDOTOXIN POLYPEPTIDE

(71) Applicant: NATIONAL TSING HUA UNIVERSITY, Hsinchu (TW)

(72) Inventors: Jya-Wei Cheng, Hsinchu (TW); Hung-Lun Chu, Hsinchu (TW); Ya-Han Chih, Hsinchu (TW); Hui-Yuan Yu, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 15/783,320

(22) Filed: Oct. 13, 2017

(65) Prior Publication Data

US 2018/0251492 A1    Sep. 6, 2018

(30) Foreign Application Priority Data

Mar. 3, 2017 (TW) .............................. 106107060 A

(51) Int. Cl.
*C07K 7/08* (2006.01)
*C07K 14/00* (2006.01)
*C07K 7/06* (2006.01)
*A61K 38/00* (2006.01)

(52) U.S. Cl.
CPC .................. *C07K 7/08* (2013.01); *C07K 7/06* (2013.01); *C07K 14/001* (2013.01); *A61K 38/00* (2013.01)

(58) Field of Classification Search
None
See application file for complete search history.

(56) References Cited

U.S. PATENT DOCUMENTS

2002/0146406 A1* 10/2002 Mayo .................... A61L 2/0088
424/94.63

* cited by examiner

*Primary Examiner* — Maury A Audet
(74) *Attorney, Agent, or Firm* — Muncy, Geissler, Olds & Lowe, P.C.

(57) ABSTRACT

An anti-endotoxin polypeptide is provided. The anti-endotoxin polypeptide having the formula (I) $A_1$-L-$C_1$, wherein $A_1$ and $C_1$ independently is a short peptide with α-helix, L is AGP (Ala-Gly-Pro) or a peptide bond, and the hydrophobicity of the hydrophobic terminus in the anti-endotoxin polypeptide is between about 0.425 and 0.765. The anti-endotoxin polypeptide of the invention can neutralize the lipopolysaccharide and has the low hemolysis and high salt resistance, simultaneously. The present invention also provides a method for design an anti-endotoxin polypeptide, the anti-endotoxic activity is adjusted through increasing and/or decreasing hydrophobicity of the hydrophobic terminal end.

3 Claims, 20 Drawing Sheets

(4 of 20 Drawing Sheet(s) Filed in Color)

Specification includes a Sequence Listing.

| Sample | Size (nm) |
|---|---|
| LPS | 168.5±1.179 |
| KR15AGP 16 µg/ml | 132.9±5.162 |
| KR12AGPKR6 16 µg/ml | 155.3±7.375 |
| KR12AGPWR6 8 µg/ml | 190.9±3.365 |
| KR12AGPWR6 16 µg/ml | 251.8±6.260 |
| KR12AGPVR6 16 µg/ml | 177.6±13.24 |

| Sample | Size (nm) |
|---|---|
| POPC/LPS | 114.3±3.402 |
| KR15AGP 16 μg/ml | 122.4±13.89 |
| KR12AGPKR6 16 μg/ml | 109.9±1.457 |
| KR12AGPWR6 8 μg/ml | 299.4±7.206 |
| KR12AGPWR6 16 μg/ml | 286.6±71.19 |
| KR12AGPVR6 16 μg/ml | 123.9±1.656 |

SEQUENCE LISTING

```
<160> NUMBER OF SEQ ID NOS: 11

<210> SEQ ID NO 1
<211> LENGTH: 12
<212> TYPE: PRT
<213> ORGANISM: Artificial Sequence
<220> FEATURE:
<223> OTHER INFORMATION: The anti-endotoxin polypeptide synthesized from
      the laboratory

<400> SEQUENCE: 1

Lys Arg Ile Val Gln Arg Ile Lys Asp Phe Leu Arg
1               5                   10

<210> SEQ ID NO 2
<211> LENGTH: 6
<212> TYPE: PRT
<213> ORGANISM: Artificial Sequence
<220> FEATURE:
<223> OTHER INFORMATION: The anti-endotoxin polypeptide synthesized from
      the laboratory

<400> SEQUENCE: 2

Arg Arg Trp Trp Arg Trp
1               5

<210> SEQ ID NO 3
<211> LENGTH: 15
<212> TYPE: PRT
```

```
<213> ORGANISM: Artificial Sequence
<220> FEATURE:
<223> OTHER INFORMATION: The anti-endotoxin polypeptide synthesized from
      the laboratory

<400> SEQUENCE: 3

Lys Arg Ile Val Gln Arg Ala Gly Pro Ile Lys Asp Phe Leu Arg
1               5                   10                  15

<210> SEQ ID NO 4
<211> LENGTH: 21
<212> TYPE: PRT
<213> ORGANISM: Artificial Sequence
<220> FEATURE:
<223> OTHER INFORMATION: The anti-endotoxin polypeptide synthesized from
      the laboratory

<400> SEQUENCE: 4

Lys Arg Ile Val Gln Arg Ile Lys Asp Phe Leu Arg Ala Gly Pro Ile
1               5                   10                  15

Lys Asp Phe Leu Arg
            20

<210> SEQ ID NO 5
<211> LENGTH: 21
<212> TYPE: PRT
<213> ORGANISM: Artificial Sequence
<220> FEATURE:
<223> OTHER INFORMATION: The anti-endotoxin polypeptide synthesized from
      the laboratory

<400> SEQUENCE: 5

Lys Arg Ile Val Gln Arg Ile Lys Asp Phe Leu Arg Ala Gly Pro Arg
1               5                   10                  15

Arg Trp Trp Arg Trp
            20

<210> SEQ ID NO 6
<211> LENGTH: 21
<212> TYPE: PRT
<213> ORGANISM: Artificial Sequence
<220> FEATURE:
<223> OTHER INFORMATION: The anti-endotoxin polypeptide synthesized from
      the laboratory

<400> SEQUENCE: 6

Lys Arg Ile Val Gln Arg Ile Lys Asp Phe Leu Arg Ala Gly Pro Arg
1               5                   10                  15

Arg Leu Val Arg Ile
            20

<210> SEQ ID NO 7
<211> LENGTH: 6
<212> TYPE: PRT
<213> ORGANISM: Artificial Sequence
<220> FEATURE:
<223> OTHER INFORMATION: A short peptide with an alpha-helix structure
      synthesized from the laboratory

<400> SEQUENCE: 7

Lys Arg Ile Val Gln Arg
1               5

<210> SEQ ID NO 8
<211> LENGTH: 12
<212> TYPE: PRT
```

```
<213> ORGANISM: Artificial Sequence
<220> FEATURE:
<223> OTHER INFORMATION: A short peptide with an alpha-helix structure
      synthesized from the laboratory

<400> SEQUENCE: 8

Lys Arg Ile Val Gln Arg Ile Lys Asp Phe Leu Arg
1               5                   10

<210> SEQ ID NO 9
<211> LENGTH: 6
<212> TYPE: PRT
<213> ORGANISM: Artificial Sequence
<220> FEATURE:
<223> OTHER INFORMATION: A short peptide with an alpha-helix structure
      synthesized from the laboratory

<400> SEQUENCE: 9

Ile Lys Asp Phe Leu Arg
1               5

<210> SEQ ID NO 10
<211> LENGTH: 6
<212> TYPE: PRT
<213> ORGANISM: Artificial Sequence
<220> FEATURE:
<223> OTHER INFORMATION: A short peptide with an alpha-helix structure
      synthesized from the laboratory

<400> SEQUENCE: 10

Arg Arg Trp Trp Arg Trp
1               5

<210> SEQ ID NO 11
<211> LENGTH: 6
<212> TYPE: PRT
<213> ORGANISM: Artificial Sequence
<220> FEATURE:
<223> OTHER INFORMATION: A short peptide with an alpha-helix structure
      synthesized from the laboratory

<400> SEQUENCE: 11

Arg Arg Leu Val Arg Ile
1               5
```

# ANTI-ENDOTOXIN POLYPEPTIDE

CROSS-REFERENCE TO RELATED APPLICATIONS

This non-provisional application claims priority under 35 U.S.C. § 119 on Patent Application No. TW106107060 filed in Taiwan, Republic of China Mar. 3, 2017, the entire contents of which are hereby incorporated by reference in its entirety.

FIELD OF THE INVENTION

The present invention relates to an anti-endotoxin polypeptide. In particular, the present invention relates to an anti-endotoxin polypeptide with helicity structure, low hemolytic activity, and high salt resistance.

BACKGROUND OF THE INVENTION

Antimicrobial peptides (AMPs) have been employed against bacterial infection in the innate defense systems of plants, insects, and animals. AMPs can target and disturb cell membrane, and hence cause the death of bacteria. The membrane lytic mechanism of AMPs makes them potential therapeutics for overcoming the antibiotic resistance.

Lipopolysaccharide (LPS, an endotoxin) is the major outer surface membrane components of gram-negative bacteria. A huge amount of LPS will be released into blood to stimulate immune response and cause sepsis when bacteria death. Human is extremely sensitive to LPS, which can cause a rise in body temperature even a very small amount of LPS (1-5 ng/kg body weight). The fever will be reduced after about 4 hours. If a patient is naturally infected with gram-negative bacteria, the fever will continue until the pathogens are completely killed because the bacteria continue to growth and release LPS. LPS can interact with macrophages to produce cytokines, such as IL-1, IL-6, and TFN-$\alpha$. These cytokines signal the hypothalamus to increase the thermal set point and cause fever.

If the antibiotic for treating the bacterial infection does not have anti-endotoxin activity, it results in shock in the patients. Therefore, it is a challenge to kill bacteria and inhibit/neutralize endotoxin simultaneously to suppress overstimulation of the immune response. An anti-endotoxin agent for neutralizing LPS and suppress immune response is required.

It is therefore attempted by the applicant to deal with the above situation encountered in the prior art.

SUMMARY OF THE INVENTION

In view of the above-mentioned problem, the present invention provides an anti-endotoxin polypeptide.

The anti-endotoxin polypeptide of the invention can target and disturb bacterial outer membrane by electrostatic effect and hydrophobicity. This mechanism is different from small molecule antibiotics. The antimicrobial peptides are deemed to have potential therapeutics for overcoming antibiotic resistance, and may replace antibiotic treatment. However, many antimicrobial peptides only kill bacteria, but do not exhibit the activity to neutralize endotoxin. Thus, how to develop an antimicrobial peptide having one (Carboxyterminus (C-terminus) or Amino-terminus (N-terminus)) amphipathic terminus and one hydrophobic terminus, and a single amino acid, peptide bound or peptide between the two termini to form the helical turn structures is an important issue. The antimicrobial peptide not only has antibacterial and anti-endotoxin activities, but also reduces over-stimulation of the immune response and inhibits inflammation. The antimicrobial peptide is safe for use and would not cause adverse reactions or side effects on organisms and humans.

The present invention provides an anti-endotoxin polypeptide having the formula (I)

$$A_1\text{-L-}C_1 \tag{I}$$

Wherein, $A_1$ and $C_1$ independently is a short peptide with an $\alpha$-helix structure in termini of the formula (I), wherein one terminus represents amphipathic and the other represents hydrophobic;

L is an oligopeptide of 1-3 amino acids in length, and L is represented by G(Gly), P(Pro), GP(Gly-Pro), or AGP(Ala-Gly-Pro), and the hydrophobicity of the hydrophobic terminal in the anti-endotoxin polypeptide is between about 0.425 and 0.765.

In one embodiment, the $A_1$ and $C_1$ independently is a short peptide of 6 to 12 amino acids.

In one embodiment, the $A_1$ is an amphipathic short peptide.

In one embodiment, the $C_1$ is a hydrophobic short peptide.

In one embodiment, the $A_1$ and $C_1$ are selected from a group consisting of KRIVQR (SEQ ID NO:7), KRIVQRIKDFLR (SEQ ID NO:8), IKDFLR (SEQ ID NO:9), RRWWRW (SEQ ID NO:10), and/or RRLVRI (SEQ ID NO:11).

In one embodiment, the $A_1$ comprises KRIVQR (SEQ ID NO:7) or KRIVQRIKDFLR (SEQ ID NO:8).

In one embodiment, the $C_1$ comprises IKDFLR (SEQ ID NO:9), RRWWRW (SEQ ID NO:10), or RRLVRI (SEQ ID NO:11).

In one embodiment, the anti-endotoxin polypeptide comprises aromatic amino acids.

In one embodiment, the anti-endotoxin polypeptide is linked to a lipopolysaccharide (LPS).

In one embodiment, the anti-endotoxin polypeptide has a high salt resistance.

The present invention further provides a novel method for designing an antimicrobial peptide with an anti-endotoxin activity. One terminus (C-terminus or N-terminus) of the antimicrobial peptide has amphipathic, and another terminus has hydrophobic. A bent hinge is located between the two termini to produce the helical turn structures, and regular the anti-endotoxin activity of the antimicrobial peptide. AGP (Ala-Gly-Pro) or a peptide chain is inserted into an antimicrobial peptide to from turning points at both N/C-terminus of the antimicrobial peptide. Thus, the antimicrobial peptide is modified to have the anti-endotoxin activity. The hydrophobic end of the antimicrobial peptide is not limited to an amino acid. For example, it also may be a hydrophobic material (long carbon chains). The length of the antimicrobial peptide is not limited. In the present invention, the minimum size required to achieve this activity is 6 amino acids, and the anti-endotoxin activity can be regulated by adjusting the parameter of hydrophobic end. The modified antimicrobial peptides also have the antibacterial and anti-inflammatory activities.

In one embodiment, the anti-endotoxin polypeptide comprises KRIVQRIKDFLR (SEQ ID NO:1), RRWWRW (SEQ ID NO:2), KRIVQRAGPIKDFLR (SEQ ID NO:3), KRIVQRIKDFLRAGPIKDFLR (SEQ ID NO:4), KRIVQRIKDFLRAGPRRWWRW (SEQ ID NO:5), or KRIVQRIKDFLRAGPRRLVRI (SEQ ID NO:6).

In one embodiment, the hydrophobic terminus in the anti-endotoxin polypeptide is between about 0.425 and 0.765.

The present invention further provide a pharmaceutical composition, comprising anti-endotoxin polypeptide having the formula (I) of $A_1$-L-$C_1$ and a pharmaceutically acceptable carrier, wherein the $A_1$ and $C_1$ independently have α-helix structure, wherein one represents amphipathic and another represents hydrophobic; L is a oligopeptide of 1-3 amino acids in length and L be represented by G(Gly), P(Pro), GP(Gly-Pro), or AGP(Ala-Gly-Pro), and the hydrophobic terminus in the anti-endotoxin polypeptide is between about 0.425 and 0.765.

Detailed description of the invention is given in the following embodiments with reference to the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
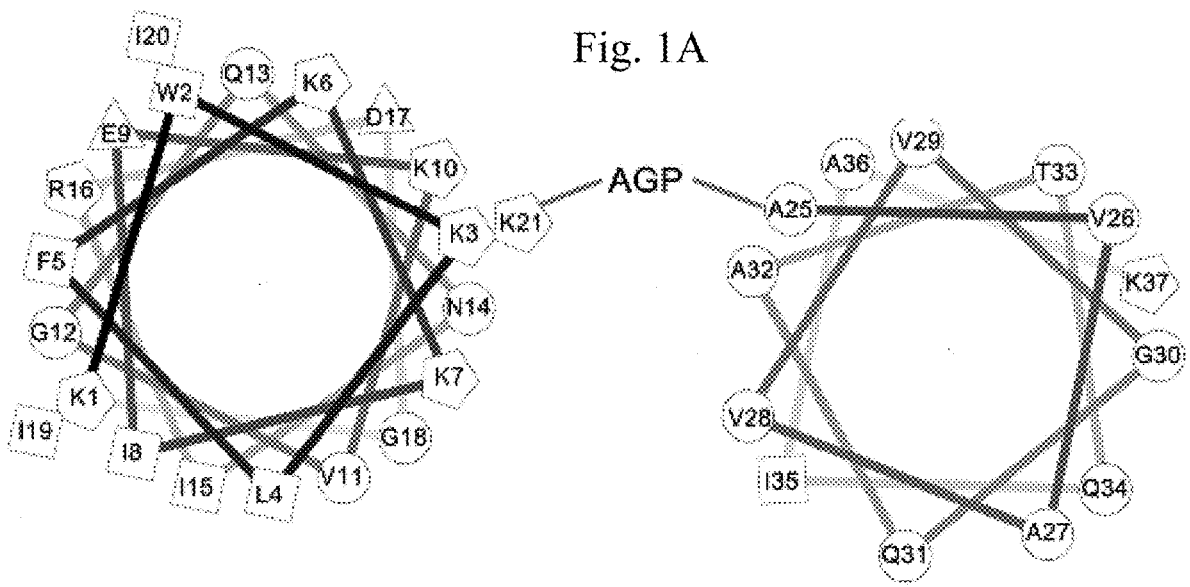
FIGS. 1A-1H illustrate the structures of anti-endotoxin polypeptides, including cecropin A (FIG. 1A), cecropin B (FIG. 1B), KR12 (FIG. 1C), WR6 (FIG. 1D), KR15AGP (FIG. 1E), KR12AGPKR6 (FIG. 1F), KR12AGPWR6 (FIG. 1G), and KR12AGPVR6 (FIG. 1H).
Figure 1B:
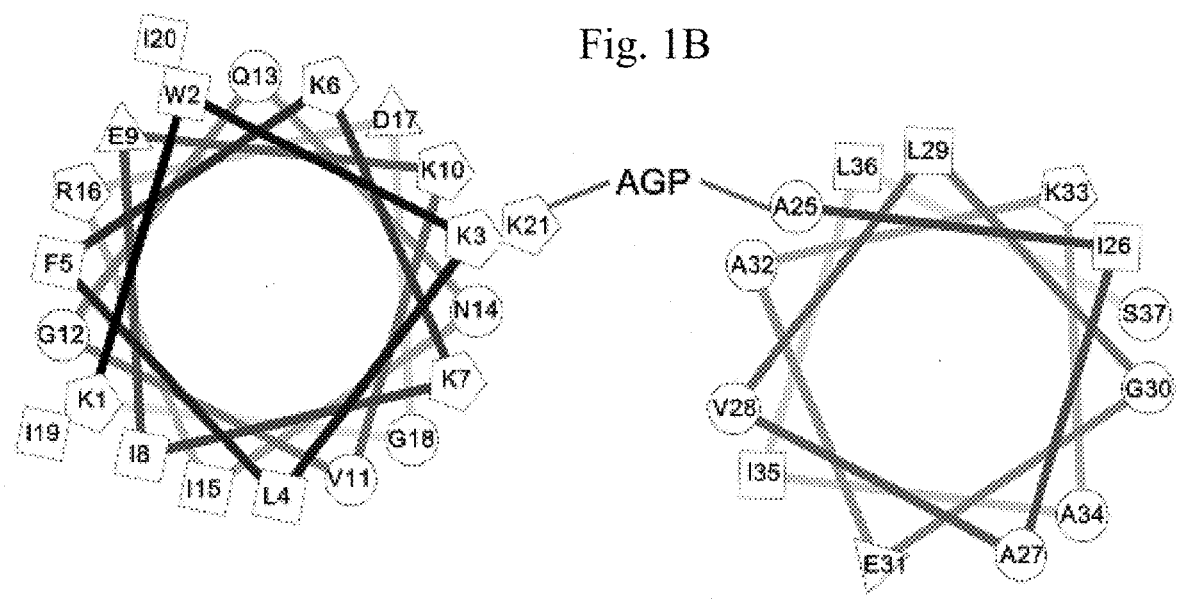
Figure 1C:
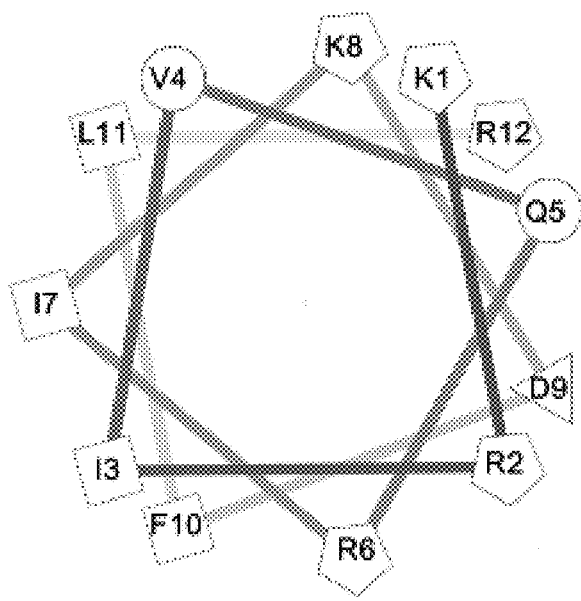
Figure 1D:
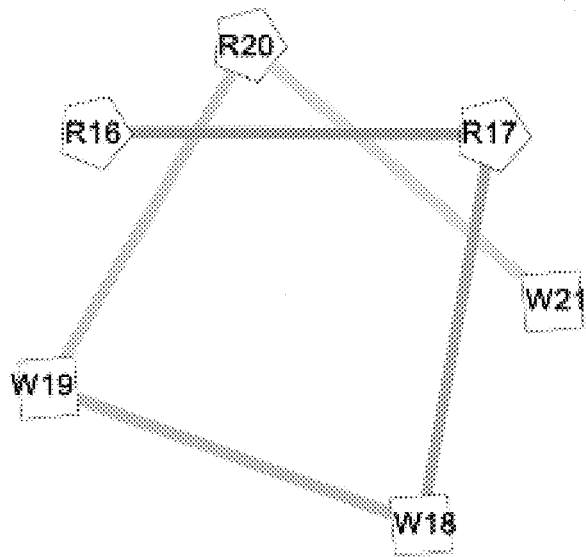
Figure 1E:
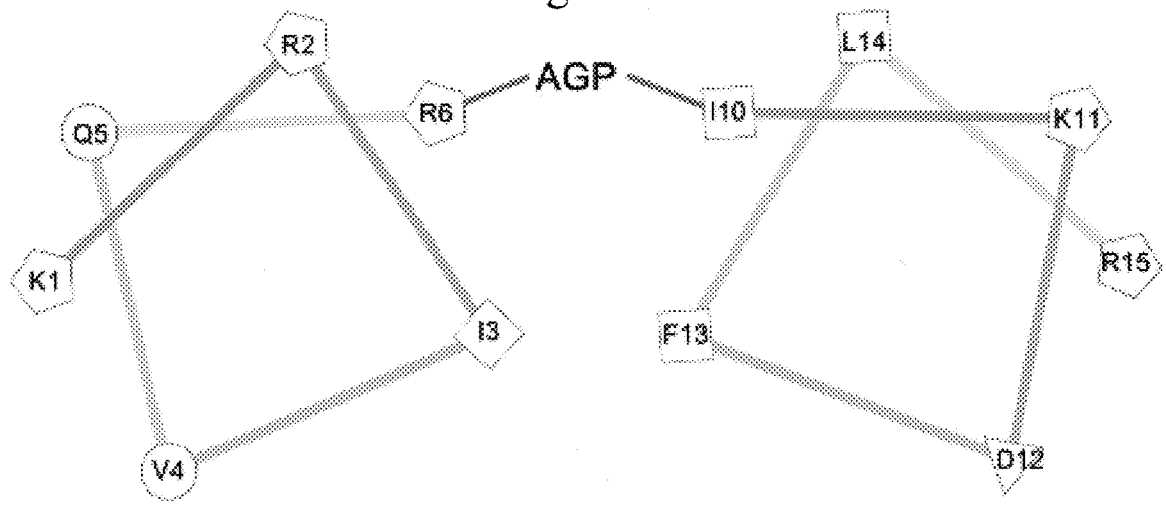
Figure 1F:
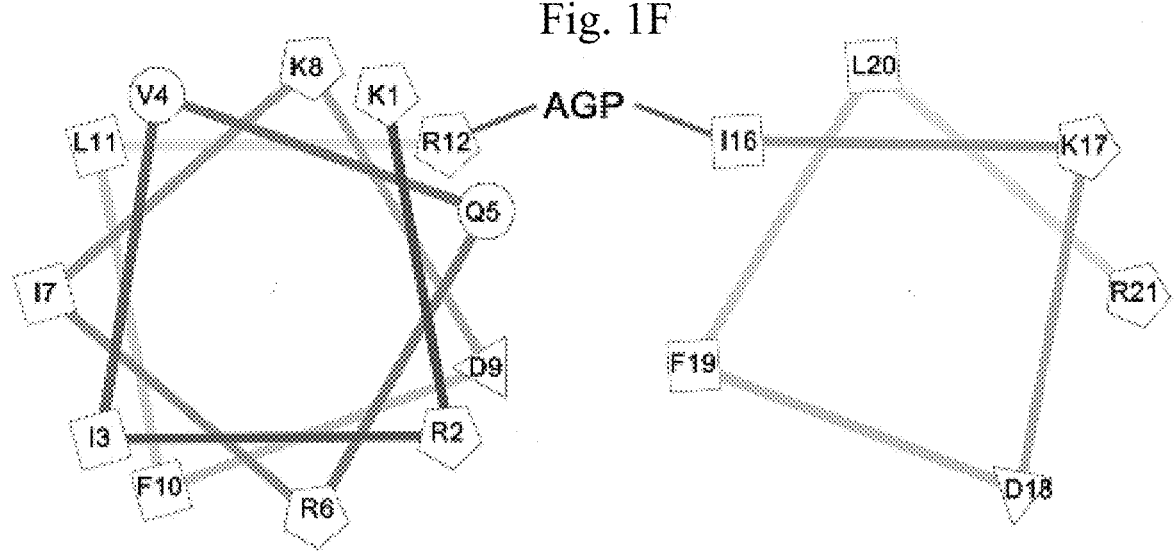
Figure 1G:
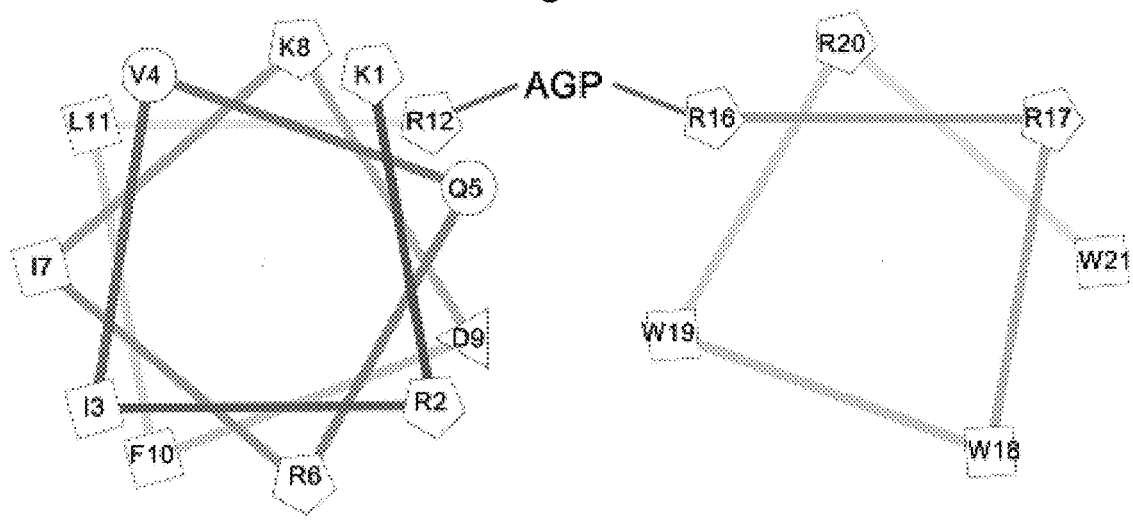
Figure 1H:
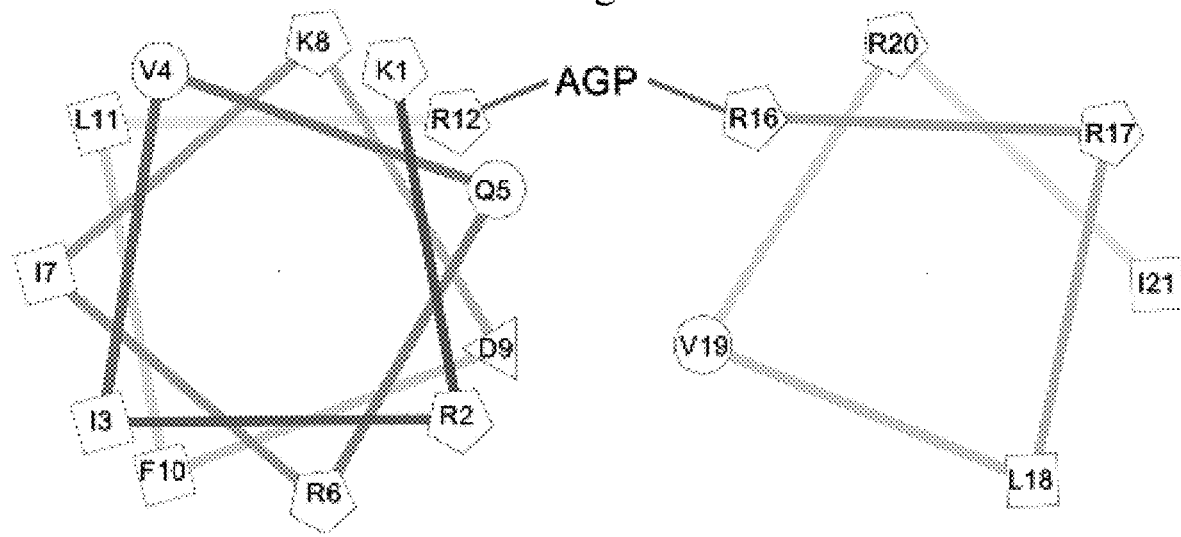

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

The present invention provides an anti-endotoxin polypeptide having the formula (I) $A_1$-L-$C_1$, wherein $A_1$ and $C_1$ independently is a short peptide with an α-helix structure in termini of the formula (I), L is a short peptide 1-3 amino acids in length of G(Gly), P(Pro), GP(Gly-Pro), or AGP (Ala-Gly-Pro).

The term "antimicrobial peptide" refers to the ability of a peptide to kill at least one bacterial species or inhibit growth of a microorganism. The antibacterial activity includes, but is not limited to anti-bacterial, anti-virus, and anti-fungal properties.

In the present invention, $A_1$ and $C_1$ are antimicrobial peptides as well known in the art or the fragments thereof, or $A_1$ and $C_1$ are N-terminus or C-terminus of an antimicrobial peptide. $A_1$ and $C_1$ independently is a short peptide with α-helix, wherein one represents amphipathic and another represents hydrophobic. In other word, if $A_1$ is an amphipathic short peptide then $C_1$ is a hydrophobic short peptide, if $A_1$ is the hydrophobic short peptide then $C_1$ is the amphipathic short peptide. In one embodiment, the antimicrobial peptide or anti-endotoxin polypeptide has about 2 to 100 amino acids, about 5 to 50 amino acids, about 6 to 25 amino acids, about 7 to 20 amino acids, preferably 6 to 12 amino acids.

In one embodiment, $A_1$ and $C_1$ include, but are not limited to KRIVQR (SEQ ID NO:7), KRIVQRIKDFLR (SEQ ID NO:8), IKDFLR (SEQ ID NO:9), RRWWRW (SEQ ID NO:10) and/or RRLVRI (SEQ ID NO:11).

The term "antibacterial activity" refers to the ability of a peptide of the invention to modify a function or metabolic process of a target microorganism, for example so as to at least partially affect replication, vegetative growth, toxin production, survival, viability in a quiescent state, or other attribute. In an embodiment, the term relates to inhibition of growth of a microorganism.

The term "microorganism" herein refers broadly to bacteria, fungi, viruses, and protozoa. In particular, the term is applicable for a microorganism having a cellular or structural component of a lipid bilayer membrane. In one embodiment, the lipid bilayer is a cytoplasmic membrane. The bacteria, fungi, viruses, and protozoa as known in the art are generally encompassed.

The length and integrity of the N-terminus and/or C-terminus of the anti-endotoxin polypeptide are very important for the antibacterial activity, because the α-helical structures of the anti-endotoxin polypeptide display the antibacterial activity.

The anti-endotoxin peptides of the invention include, but are not limited to KRIVQRAGPIKDFLR (SEQ ID NO:3), KRIVQRIKDFLRAGPIKDFLR (SEQ ID NO:4), KRIVQRIKDFLRAGPRRWWRW (SEQ ID NO:5), or KRIVQRIKDFLRAGPRRLVRI (SEQ ID NO:6), preferably KRIVQRIKDFLRAGPRRWWRW (SEQ ID NO:5).

It shall be noted that the anti-endotoxin polypeptides of the invention have hydrophobic and aromatic amino acids. In one embodiment, the hydrophobicity of the hydrophobic terminus in the anti-endotoxin polypeptide is between about 0.425 and 0.765. In another embodiment, the anti-endotoxin polypeptides of the present invention have aromatic amino acids, such as phenylalanine, tryptophan and/or tyrosine.

The anti-endotoxin polypeptide display random structure in solutions or mammalian cells. The amphipathic structure of the anti-endotoxin polypeptide can be bound to LPS through charges to form an α-helix structure. The hydrophobic arm is inserted into LPS by hydrophobic interactions with lipid A region. Therefore, the blocked lipid A region and aggregated LPS vesicles wouldn't cause LPS-induced inflammation.

Additionally, the anti-endotoxin peptides of the present invention have a low hemolytic activity and a high salt resistance, simultaneously.

The present invention further provides a novel method for designing an antimicrobial peptide with an anti-endotoxin activity. One terminus (C-terminus or N-terminus) of the antimicrobial peptide has amphipathic, and another terminus has hydrophobic. A bent hinge is located between the two termini to produce the helical turn structures, and therefore, the anti-endotoxin activity of the polypeptide of the present invention can be regulated. AGP (Ala-Gly-Pro) or a peptide chain is inserted into two adjacent residues of an antimicrobial peptide to form turning points at both N/C-termini of the antimicrobial peptide. Thus, after modification, the antimicrobial peptide without the anti-endotoxin activity is changed to have the anti-endotoxin activity. The hydrophobic end of the antimicrobial peptide is not limited to an amino acid, may be a hydrophobic material (long carbon chains). The length of the antimicrobial peptide is also not limited. In the present invention, the minimum size required to achieve this activity is 6 amino acids, and the anti-endotoxin activity can be regulated by adjusting the parameter of hydrophobic end, which is related to the length of amino acids. The modified antimicrobial peptides also have the antibacterial and anti-inflammatory activities.

The present invention further provides a pharmaceutical composition comprises the anti-endotoxin polypeptide of the present invention and a pharmaceutically acceptable carrier.

The term "pharmaceutically acceptable carrier" as used herein means a pharmaceutically-acceptable material, composition or vehicle, such as a liquid or solid filler, diluent, excipient, solvent or encapsulating material, involved in carrying or transporting a anti-endotoxin polypeptide of the present invention from one location, body fluid, tissue, organ, or portion of the body, to another location, body fluid, tissue, organ, or portion of the body.

Some examples of materials which can serve as pharmaceutically-acceptable carriers include sugars, starches, cellulose, powdered tragacanth, malt, gelatin, talc, excipients, oils, glycols, polyols, esters, agar, buffering agents, alginic acid, pyrogen-free water, isotonic saline, Ringer's solution, ethyl alcohol, phosphate buffer solutions, other non-toxic compatible substances employed in pharmaceutical formulations.

Additional specific embodiments of the present invention include, but are not limited to the following:

Example 1

Design of Anti-Endotoxin Peptide

In this embodiment, LPS-inactive α-helical peptide KR12 (SEQ ID NO:1) and WR6 (SEQ ID NO:2) were used as N-terminus and C-terminus, respectively to form the anti-endotoxin polypeptide of the present invention. The anti-endotoxin polypeptide of the present invention comprised KR15AGP (SEQ ID NO:3), KR12AGPKR6 (SEQ ID NO:4), KR12AGPWR6 (SEQ ID NO:5), and KR12AGPVR6 (SEQ ID NO:6) as shown in Table 1.

TABLE 1

The anti-endotoxin polypeptide of the present invention.

| Name | Sequence | SEQ ID NO | Charge | Mw |
|---|---|---|---|---|
| KR12 | KRIVQRIKDFLR | 1 | +4 | 1517.93 |
| WR6 | RRWWRW | 2 | +3 | 1045.22 |
| KR15AGP | KRIVQRAGPIKDFLR | 3 | +4 | 1838.25 |
| KR12AGPKR6 | KRIVQRIKDFLRAGPIKDFLR | 4 | +4AGP+1 | 2611.2 |
| KR12AGPWR6 | KRIVQRIKDFLRAGPRRWWRW | 5 | +4AGP+3 | 2865.46 |
| KR12AGPVR6 | KRIVQRIKDFLRAGPRRLVRI | 6 | +4AGP+3 | 2632.27 |

AGP was inserted into two adjacent residues of KR12 to form KR15AGP. KR12AGPKR6, KR12AGPWR6, and KR12AGPVR6 employed KR12 as the amphipathic N-terminal α-helix structure, and three kinds of α-helix structures at C-terminus were used to estimate the hydrophobic effect of the anti-endotoxin (FIG. 1).

Example 2

Antibacterial Activity and Salt Resistance

The antibacterial activities were determined by the standard broth microdilution method of National Committee for Clinical Laboratory Standards with the MH and LYM broth. MH or LYM broth with 50, 100, 200, or 300 mM NaCl (containing 5.4 mM KCl, 5.6 mM $Na_2HPO_4$, 0.5 mM $MgSO_4$, and 1.0 mM sodium citrate, 0.4 mg of $ZnCl_2$, 2.0 mg of $FeCl3.6H_2O$, 0.1 mg of $CuSO4.5H_2O$, 0.1 mg of $MnSO_4.H_2O$, 0.1 mg of $Na_2B_4O_7.10H_2O$, 700 mg of amino acid mixtures without tryptophan (Clontech), and 20 mg of L-Tryptophan, 2% vitamin mixture (100×, Sigma) and glucose at final concentration of 2%) were used to serially dilute the anti-endotoxin polypeptide of the present invention to obtain anti-endotoxin polypeptide solutions with a concentration ranging from 3,200 to 100 μg/mL.

Figure 2:
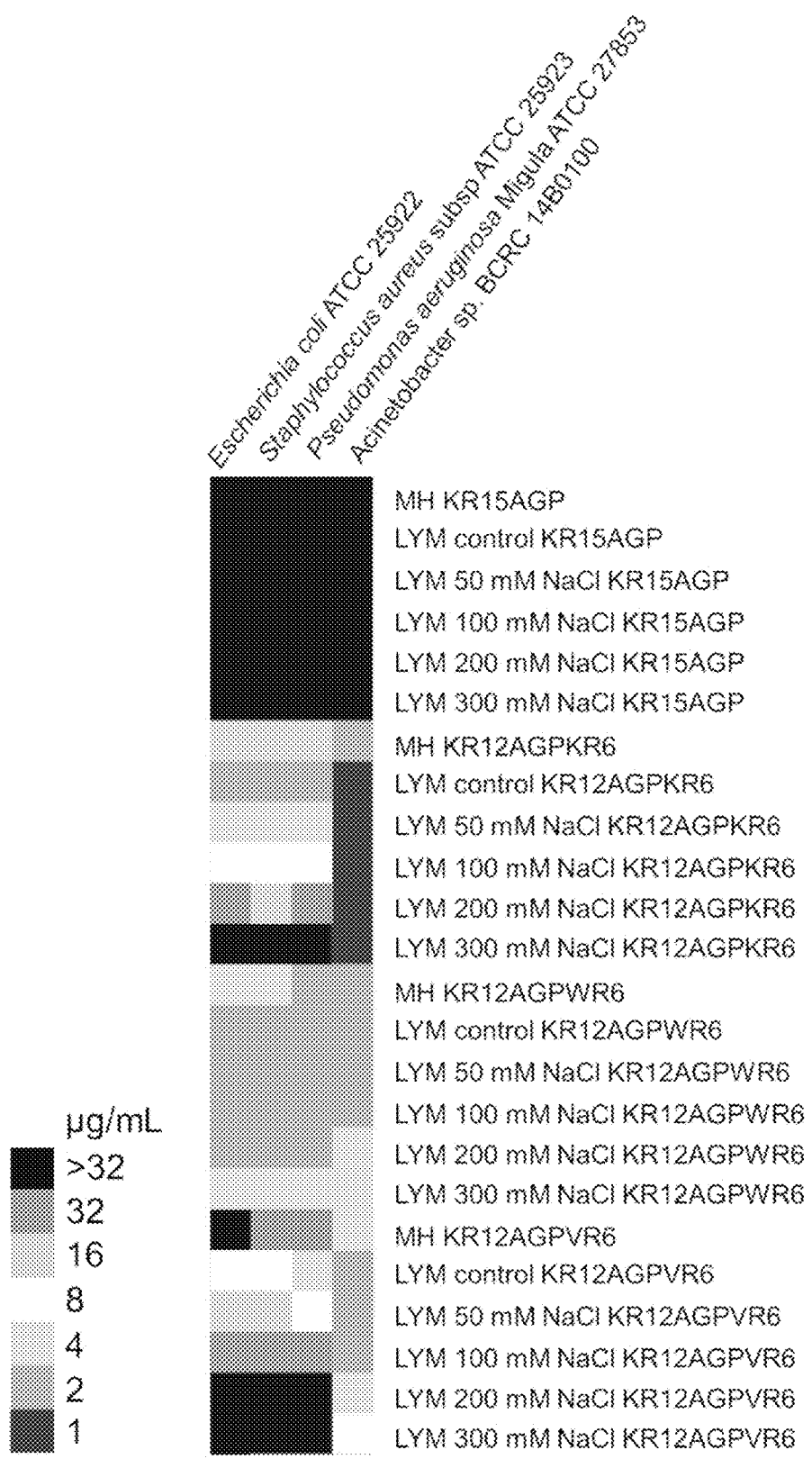
FIG. 2 illustrates the minimum inhibitory concentration (MIC) of KR15AGP, KR12AGPKR6, KR12AGPWR6, and KR12AGPVR6.

1 μL of peptide solutions were mixed with 99 μL inoculums ($5 \times 10^5$ CFU/mL) in polypropylene 96-well plates, respectively. The turbidity at OD600 nm was determined by ELISA plate reader (Thermo Max, Molecular Devices, Sunnyvale, Calif.). The absorbance of culture medium and inoculum without peptides were used as the negative and positive control, respectively. The minimum inhibitory concentration (MIC) values were converted to a color scale and displayed using the Tree View Program. All peptides were tested in triplicate. Referring to FIG. 2, KR15AGP peptide did not show any activity against gram-positive and negative bacteria in MH or LYM broth. KR12AGPKR6 peptide was very effective against bacteria in LYM broth condition (MIC=about 2 µg/mL). However, the MIC values of KR12AGPKP6 were increased to about 16 µg/mL in broth with 200 mM NaCl. On the other hand, KR12AGPKR6 was inactive totally at 300 mM salt condition.

KR12AGPWR6 displayed superior antibacterial activities against gram-positive and negative bacteria in high salt conditions (MIC=about 2-4 µg/mL). KR12AGPVR6 also showed high activities under low NaCl condition, but lost its activities at 200 mM NaCl. Compared to other bacteria strain, KR12AGPKR6, KR12AGPWR6, and KR12AGPVR6 were more effective to *Acinetobacter* sp.

Overall, the degree of antibacterial activities and salt resistances of anti-endotoxin polypeptide were KR12AGPWR6>KR12AGPKR6>KR12AGPVR6>KR15AGP.

Example 3

Binding and Neutralization of Peptide to Endotoxin

The abilities of the anti-endotoxin polypeptides to bind and neutralize LPS were assessed using Limulus Amebocyte Lysate (LAL) assay (Cape Cod Inc, East Falmouth, Mass., USA). 25 µL of different peptide concentration (128, 64, 32, 16, and 8 µg/mL) were mixed with 25 µL CSE (Control Standard Endotoxin) (5EU) in a 96-well plate, and 50 µL of Pyrochrome® reagent was added to wells immediately. The absorbance at 405 nm was measured by microplate reader at 37° C. for 25 minutes.

Figure 3:
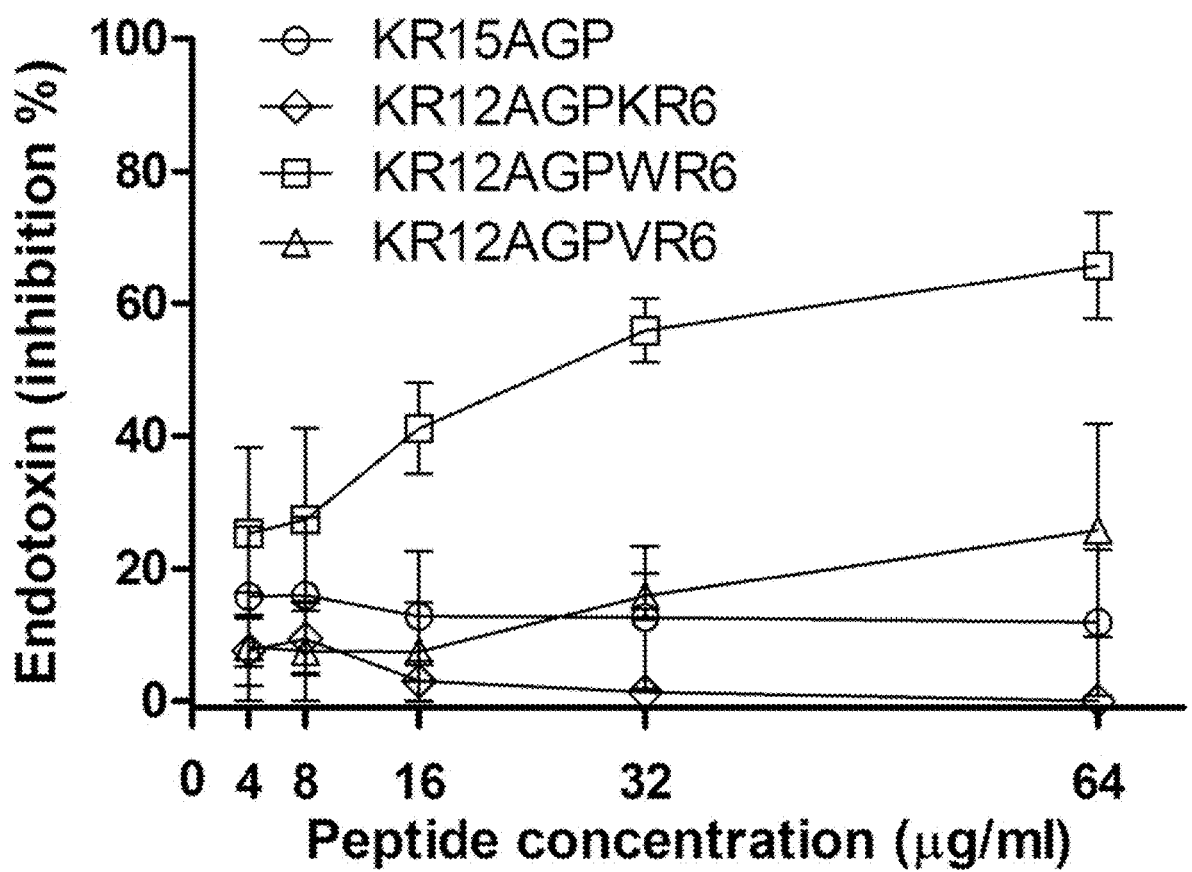
FIG. 3 illustrates the LPS-neutralizing activities. KR12AGPWR6 peptide (□) has a better LPS-neutralizing activity.

Referring to FIG. 3, KR12AGPWR6 could block the interaction between LPS and factor C, and neutralize downstream reaction dose-dependently. Nevertheless, KR15AGP, KR12AGPKR6 and KR12AGPVR6 had only small effects.

Example 4

Cytotoxicity Test

In this embodiment, the cytotoxicity was evaluated by MTT assay. J744A.1 cells were seeded in a 96-well plate with $10^4$ cells/100 µL/well and incubated for 24 hours. After removing the medium, 100 µL of fresh medium containing anti-endotoxin polypeptide (2 to 64 µg/mL) was added to the wells. After 24 hours incubation, the fresh medium with 0.5 mg/mL MTT was added and incubated for 3 hours. After the medium/MTT was removed, DMSO was added at 100 µL for dissolving the formazan crystal. Cell survival rate was calculated by measuring the absorbance at 450 nm using Multi-labeled Microplate Reader (VICTOR 3).

Figure 4:
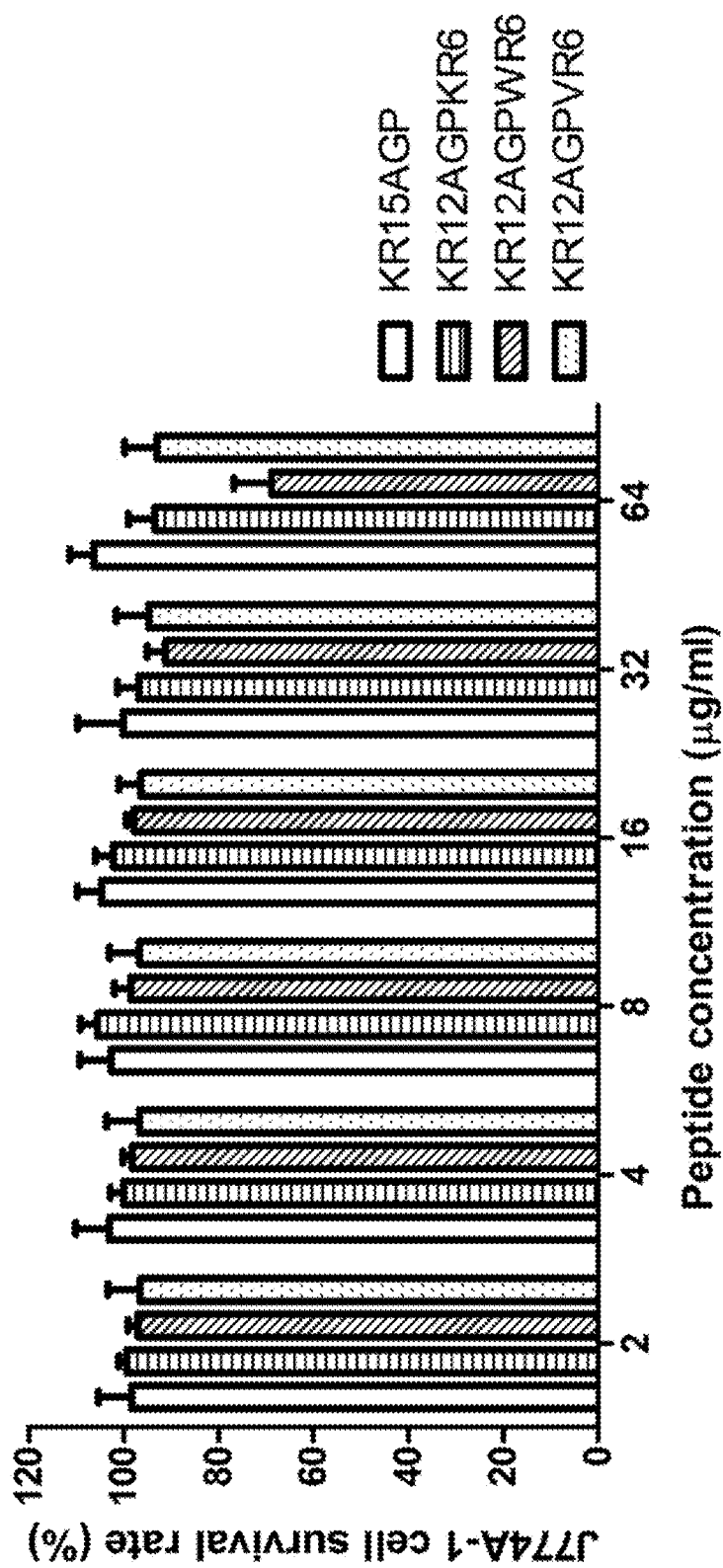
FIG. 4 illustrates the cytotoxicity of the anti-endotoxin polypeptides.

Referring to FIG. 4, all four polypeptides were not showed toxicities under the concentration of 32 µg/mL. K12AGPWR6 was showed light toxicity (survival rate=about 70%) on the concentration of 64 µg/mL.

Example 5

Peptide-Induced Permeabilization of Large Unilamellar Vesicles

In this embodiment, the large unilamellar vesicles (LUVs) of POPC/LPS (POPC:LPS=12.5:1 mol/mol), POPC/cholesterol (POPC:cholesterol=2:1 mol/mol), and POPC:POPG (POPC:POPG=3:1 mol/mol) were prepared by the extrusion method with Avanti small-volume extrusion apparatus (Avanti Polar Lipid). Calcein-filed LUVs were prepared by calcein-containing buffer (70 mM calcein and 10 mM Tris at pH 7.4). Peptide-induced calcein leakages were measured by Perkin-Elmer luminescence spectrofluorimeter at excitation and emission wavelengths of 496 and 515 nm, respectively. Leakage is expressed as a percentage relative to the total amount of dye released by addition of 100 mg/mL of Triton X-100, which represented 100% leakage (the maximum fluorescence intensity).

The degree of leakage induced by various concentrations of polypeptides was estimated by: % leakage=$(F-F_0)/(Fr-F_0) \times 100\%$, wherein the $F_0$ is the initial fluorescence intensity observed without peptide, and Fr is the fluorescence intensity of 100% leakage.

Figure 5A:
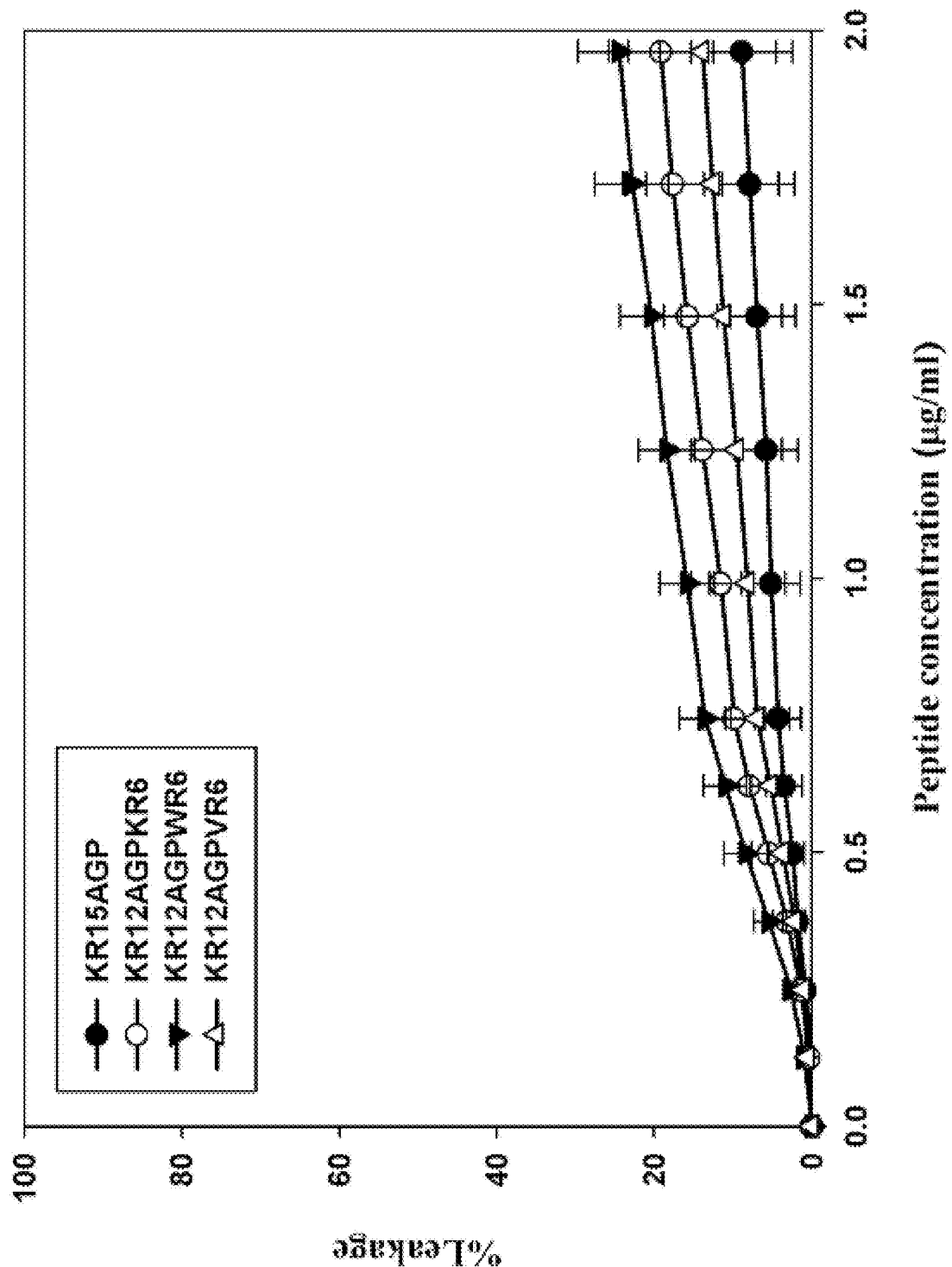
FIGS. 5A-5C illustrate the peptide-induced permeabilization of large unilamellar vesicles (LUVs). All four peptides display weak leakages on POPC/cholesterol LUVs (FIG. 5A). KR12AGPKR6, KR12AGPWR6, and KR12AGPVR6 show leaking activities on POPC/LPS and POPC/POPG LUVs (FIGS. 5B-5C).
Figure 5B:
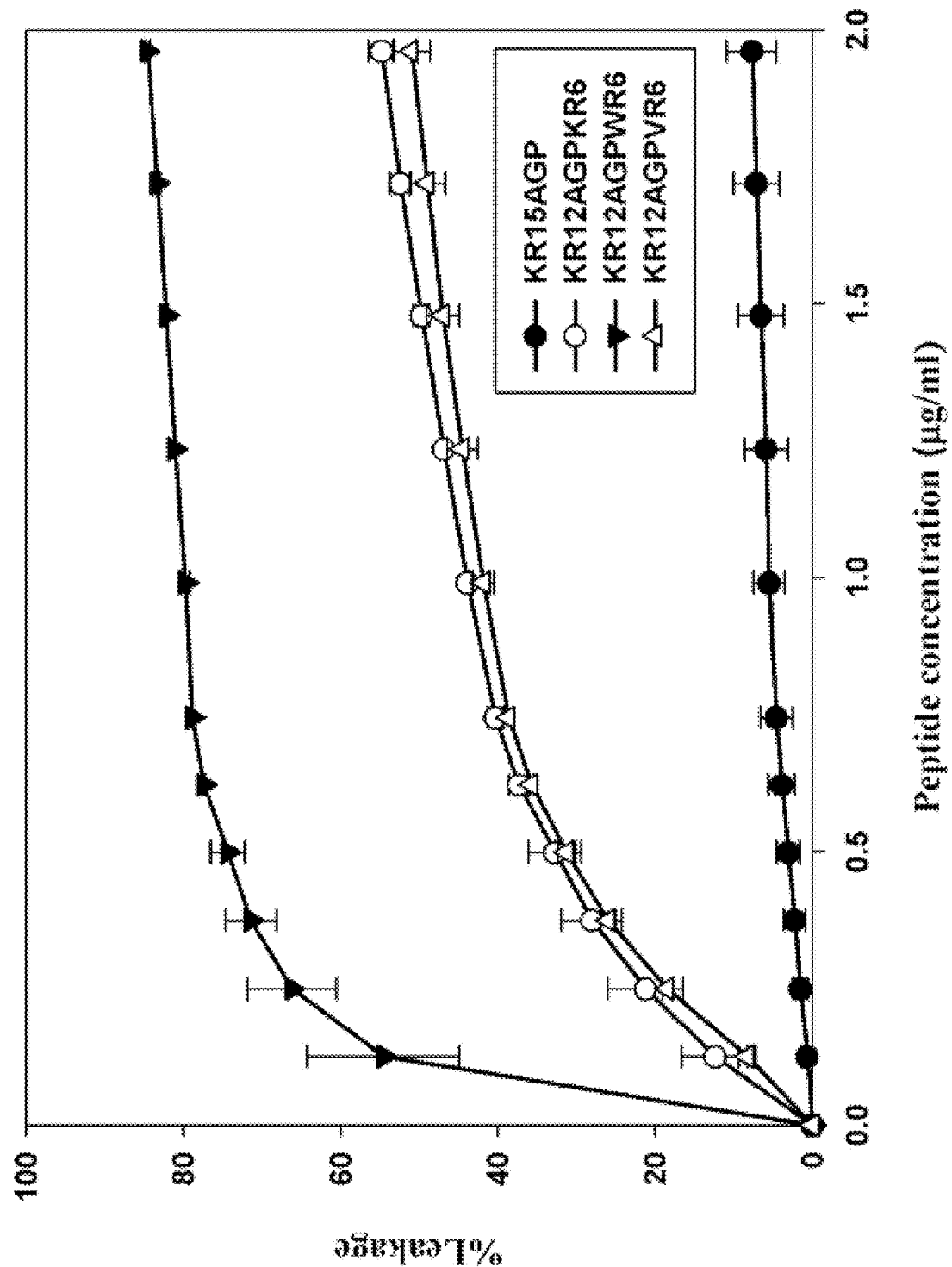
Figure 5C:
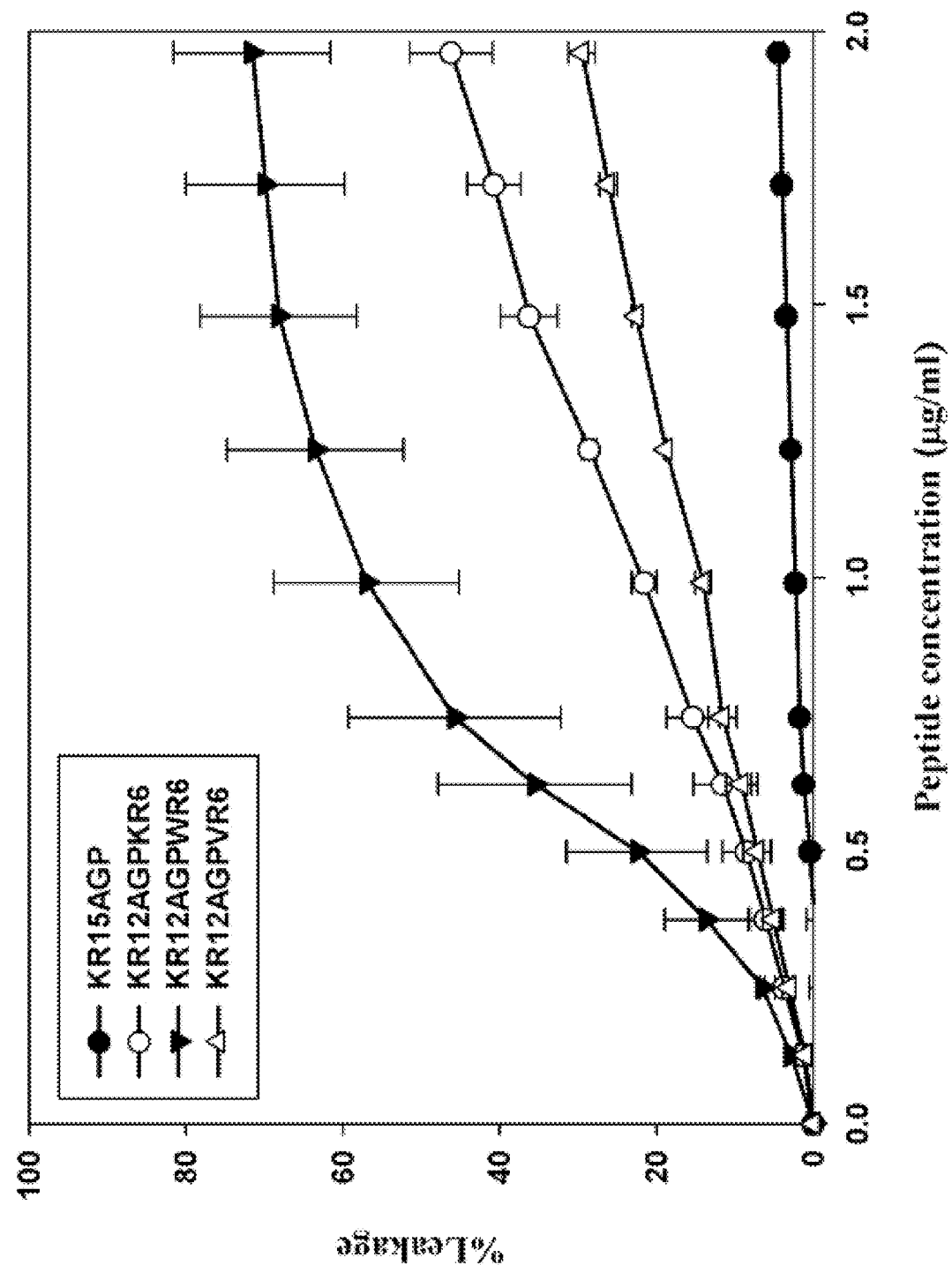
Figure 6A:
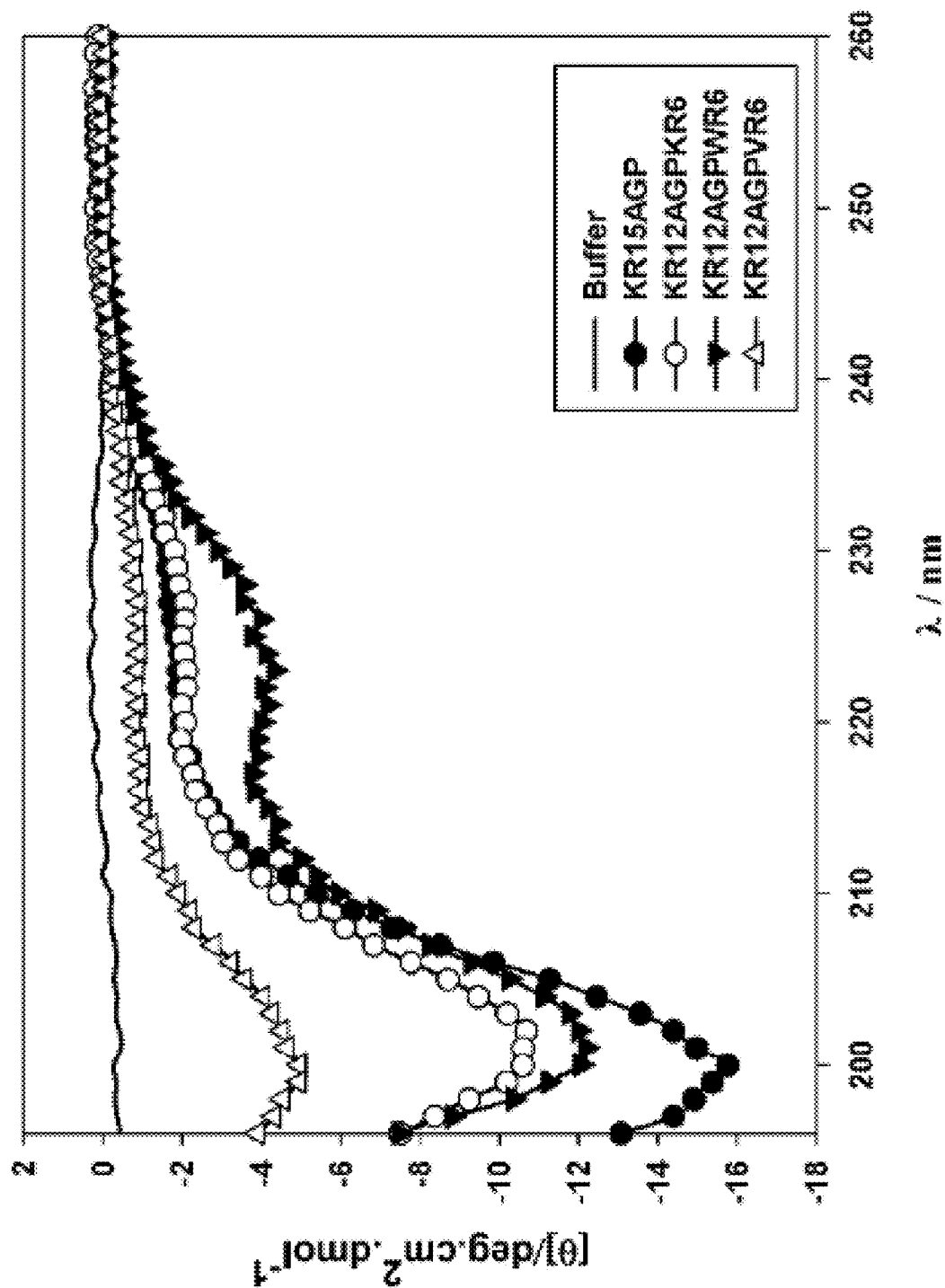
FIGS. 6A-6E illustrate the random structure of the polypeptides of the invention in phosphate buffer (FIG. 6A), TE buffer (FIG. 6B), POPC/Cholesterol (FIG. 6C), POPC/LPS (FIG. 6D), and POPC/POPG (FIG. 6E).
Figure 6B:
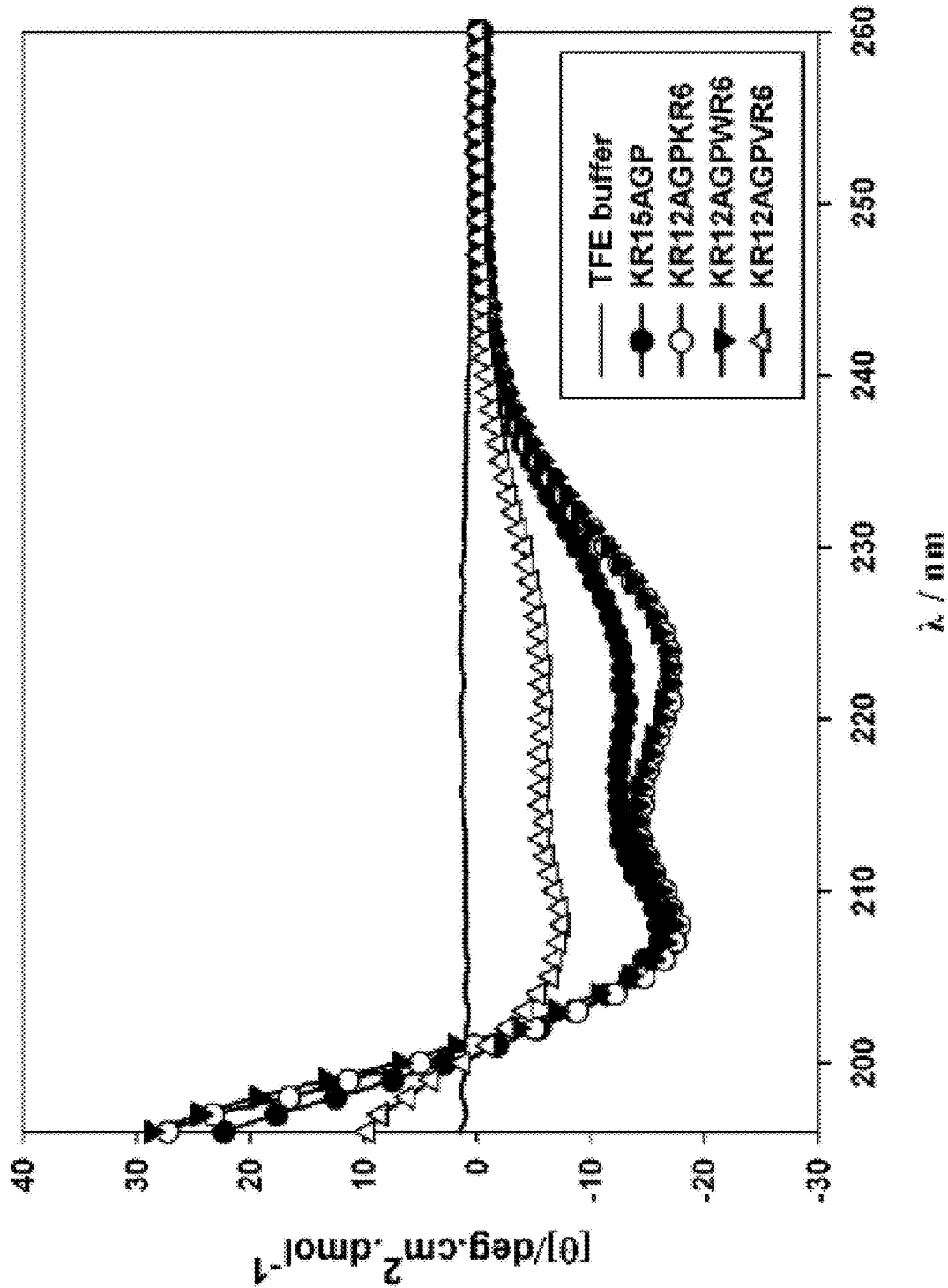
Figure 6C:
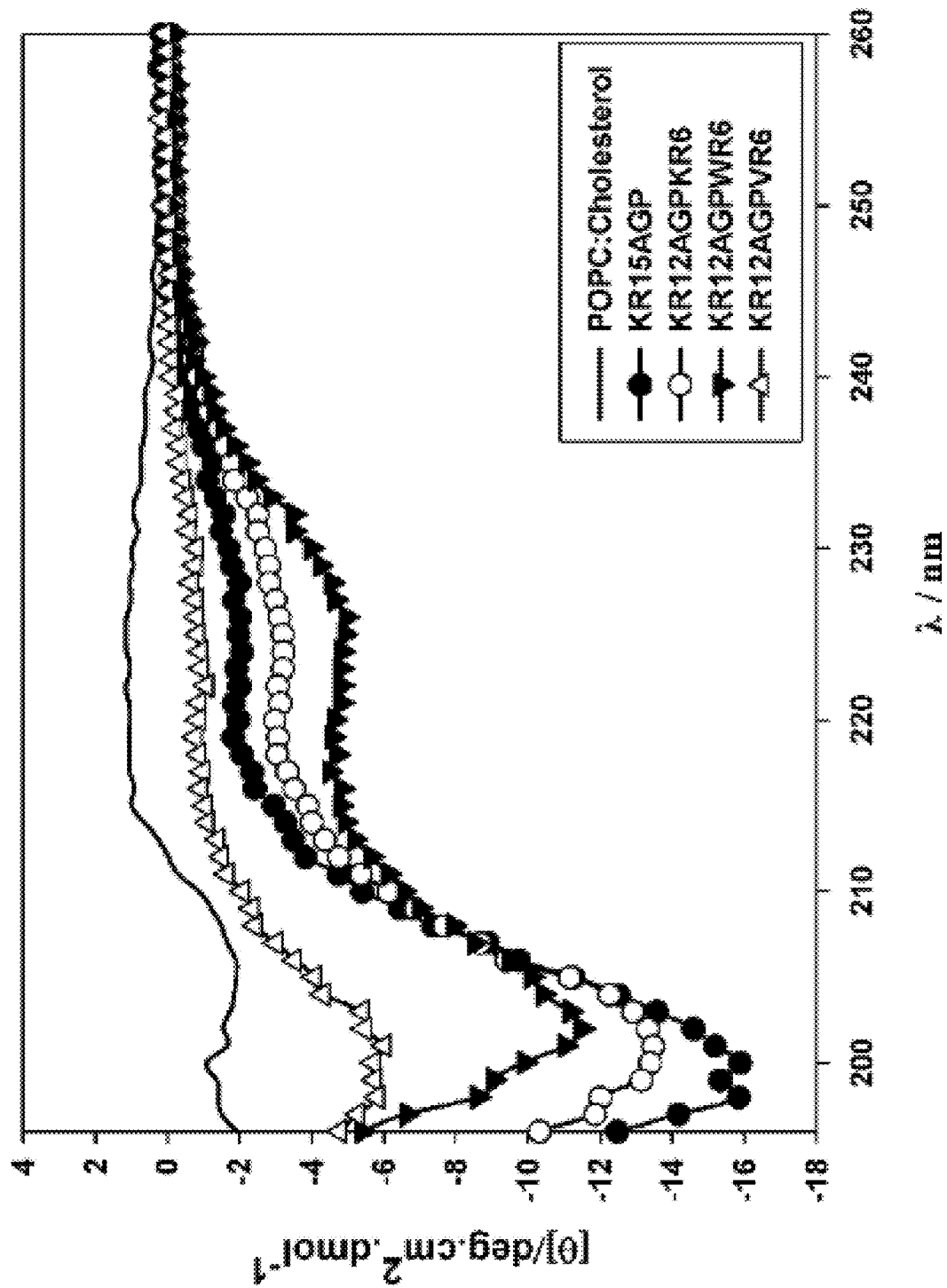
Figure 6D:
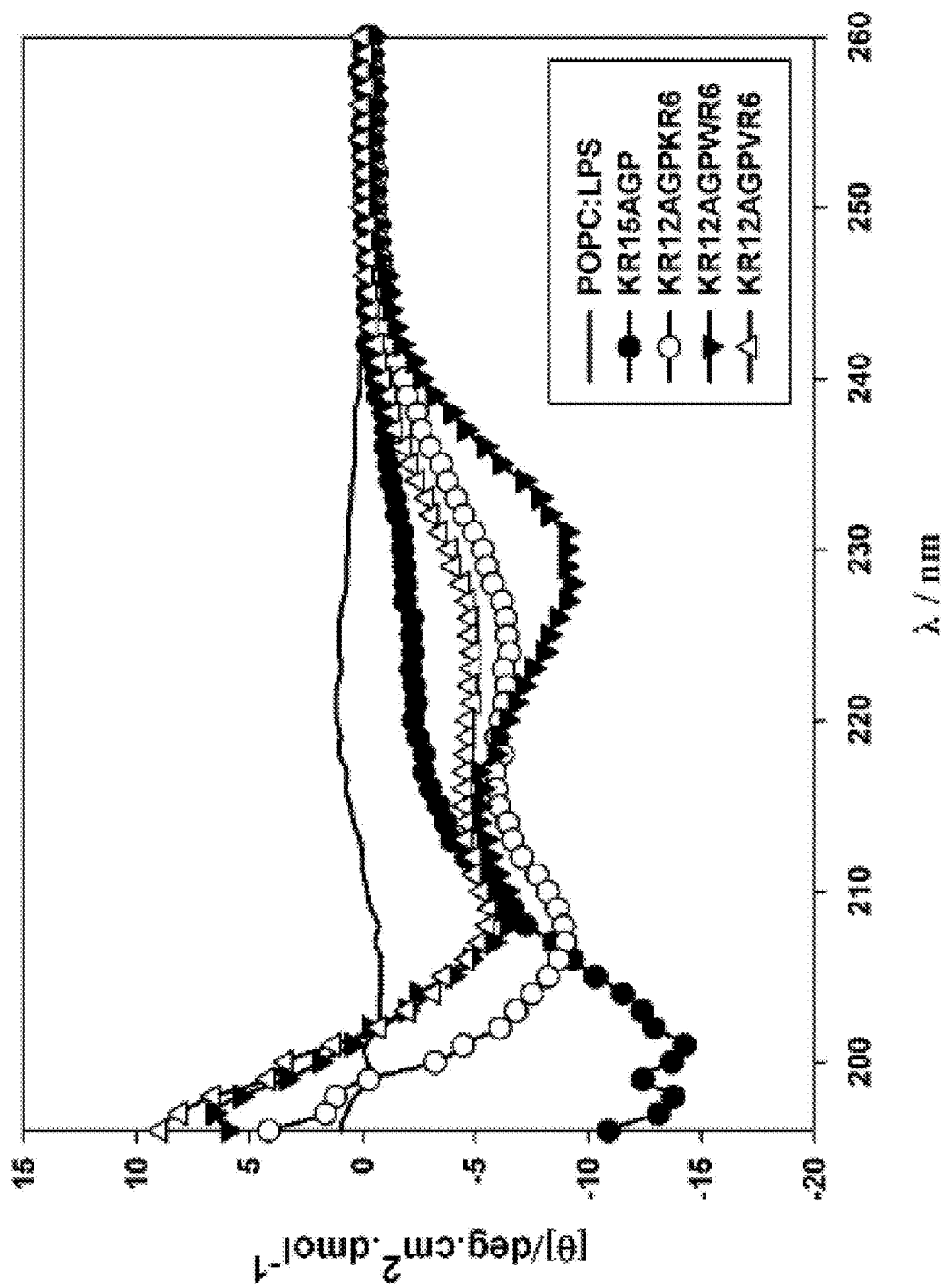
Figure 6E:
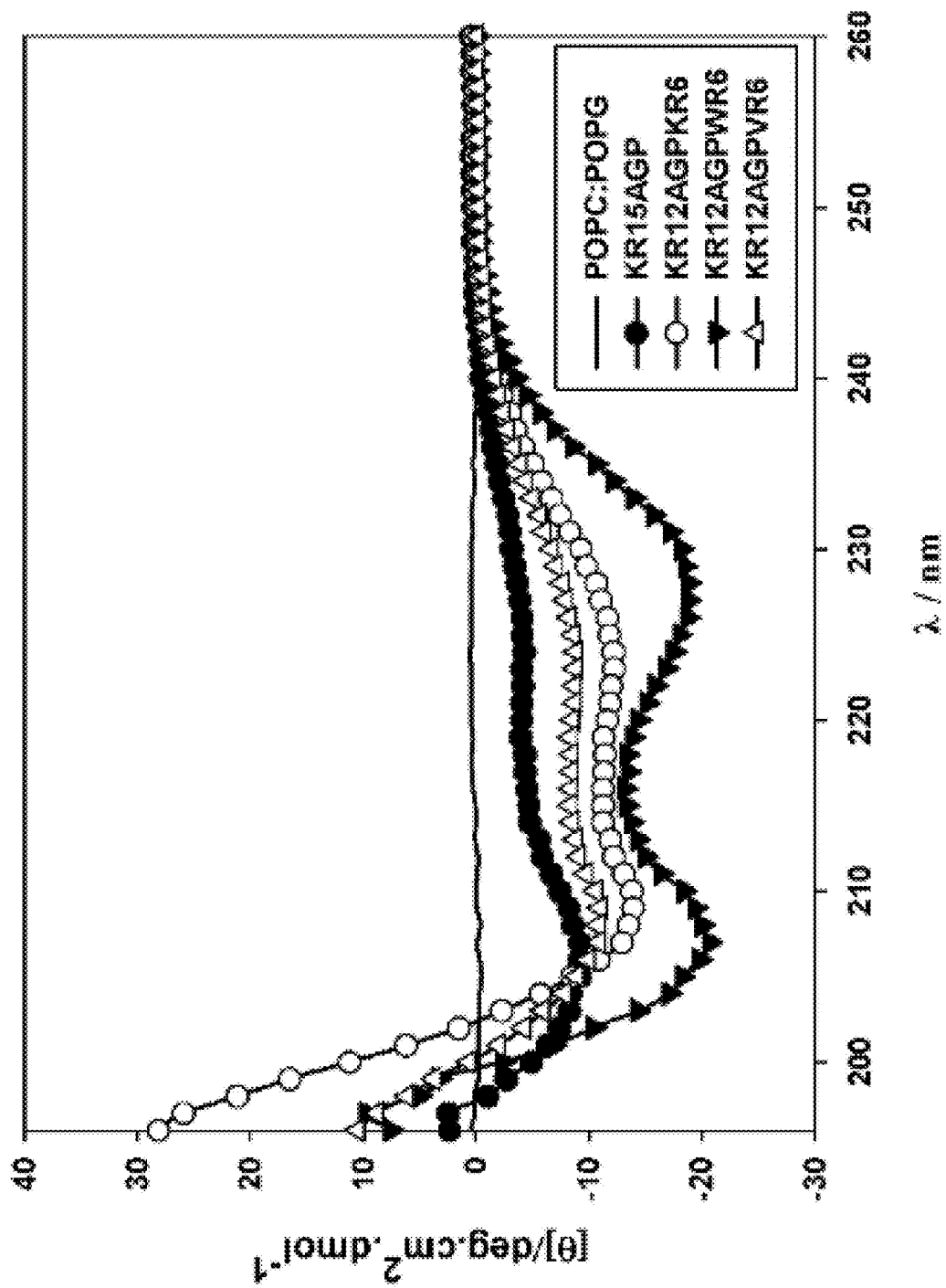

Referring to FIG. 5, all four polypeptides displayed weak leakages on POPC/cholesterol LUVs (FIG. 5A). KR12AGPKR6, KR12AGPWR6, and KR12AGPVR6 showed does-dependent calcein leaking activities on POPC/LPS and POPC/POPG LUVs (FIG. 5B-5C). KR12AGPWR6 demonstrated the strongest calcein leakage on POPC/LPS and POPC/POPG LUVs with about 80% and 70%, respectively. The results indicate that the activities of the polypeptides to induce calcein release on negatively charged LUVs were concordant with their antibacterial activities.

Example 6

Circular Dichroism Spectroscopy

In this embodiment, the circular dichroism (CD) spectra were recorded with an AVIV 202 spectropolarimeter after calibration with d-10-camphorsulfonic acid to determine the secondary structure of the peptides. The peptides were diluted with phosphate buffer to a concentration of 60 mM to 1 mM, and scanned wavelength from 190 to 260 nm.

Referring to FIG. 6, all four polypeptides were displayed random structure in phosphate buffer and POPC/Cholesterol. The conformational change to form α-helical structures was found in TFE, POPC/LPS, and POPC/POPG environments except for KR15AGP. The degree of helicity in POPC/LPS and POPC/POPG environment was found to be KR12AGPWR6>KR12AGPKR6>KR12AGPVR6>KR15AGP. The results show that the helicity contents of the anti-endotoxin polypeptide in negatively charged membrane models were concordant with their antibacterial activities.

Example 7

LPS Aggregation

The LPS molecule were dissolved in chloroform:methanol (2:1) then the stock solution was sonicated at 40° C. for 20 minutes and then kept at 4° C. overnight. The stock solution were diluted to 25 µM by using 20 mM sodium phosphate buffer with 150 mM sodium chloride and then at 4° C. overnight for use. Peptide concentration was diluted to 8 or 16 µg/mL. After the LPS solution was interacted with the peptide solution, the particle size and distribution analysis was measured by dynamic light scattering in Malvern Zetasizer ZS (Malvern, UK).

Figure 7A:
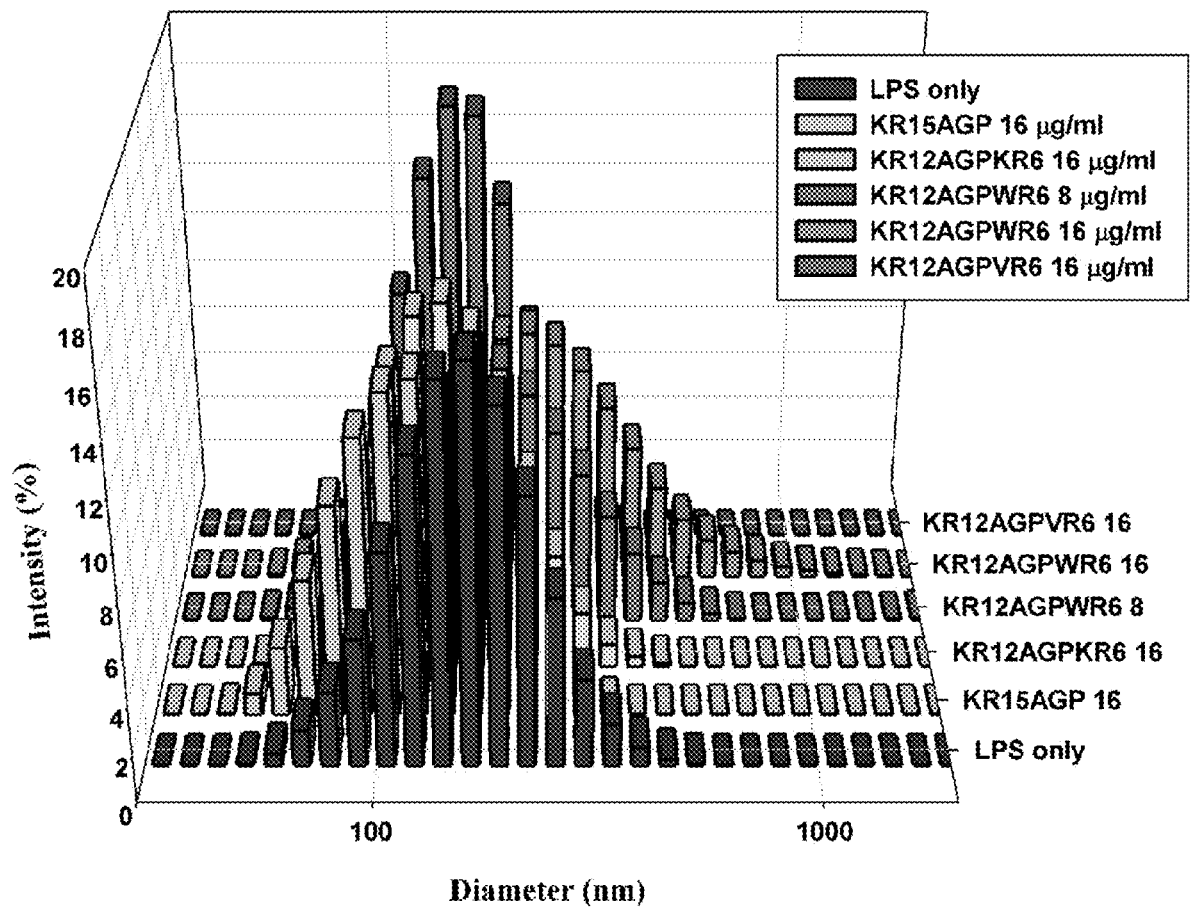
FIGS. 7A-7B illustrate the distribution of LPS aggregates in the presence of the anti-endotoxin polypeptides of the invention.
Figure 7B:
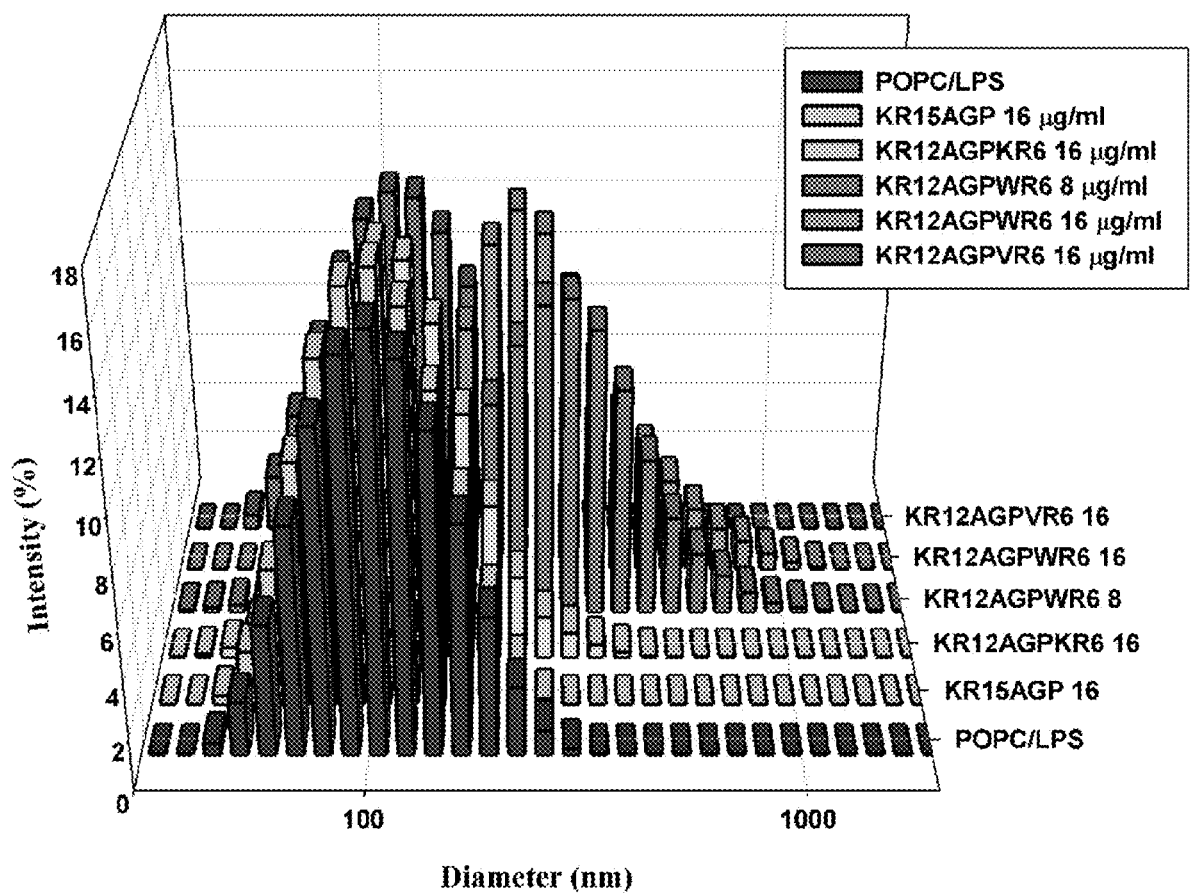

Referring to FIG. 7, 8 and 16 µg/mL of KR12AGPWR6 promoted LPS (FIG. 7A) and POPC/LPS LUVs (FIG. 7B) aggregation and increased their mean particle sizes. KR15AGP, KR12AGPKR6, and KR12AGPVR6 did not aggregate LPS and change particle size.

Example 8

Inhibition of Endotoxin-Induced Inflammatory

J744A.1 cells ($3 \times 10^5$ cells) were seeded in a 24-well plate and incubated for 24 hours. Cells were washed by PBS and LPS (*E. coli* 026:B6 (SIGMA, 150 ng/mL)) and the anti-endotoxin polypeptide of the present invention (2-32 μg/mL) were added to the wells. After 24 hours treatment, culture supernatant was harvested and centrifuged at 1,000 rpm for 10 minutes. 50 μL of culture supernatant was mixed with 50 μL Griess reagent (SIGMA) in a 96-well plate and incubated at room temperature for 10 minutes. The absorbance at 540 nm was measured and the NO concentration was calculated. Additionally, the concentration of TNF-α in the culture supernatant was evaluated using ELISA kits (eBiosciences).

Figure 8A:
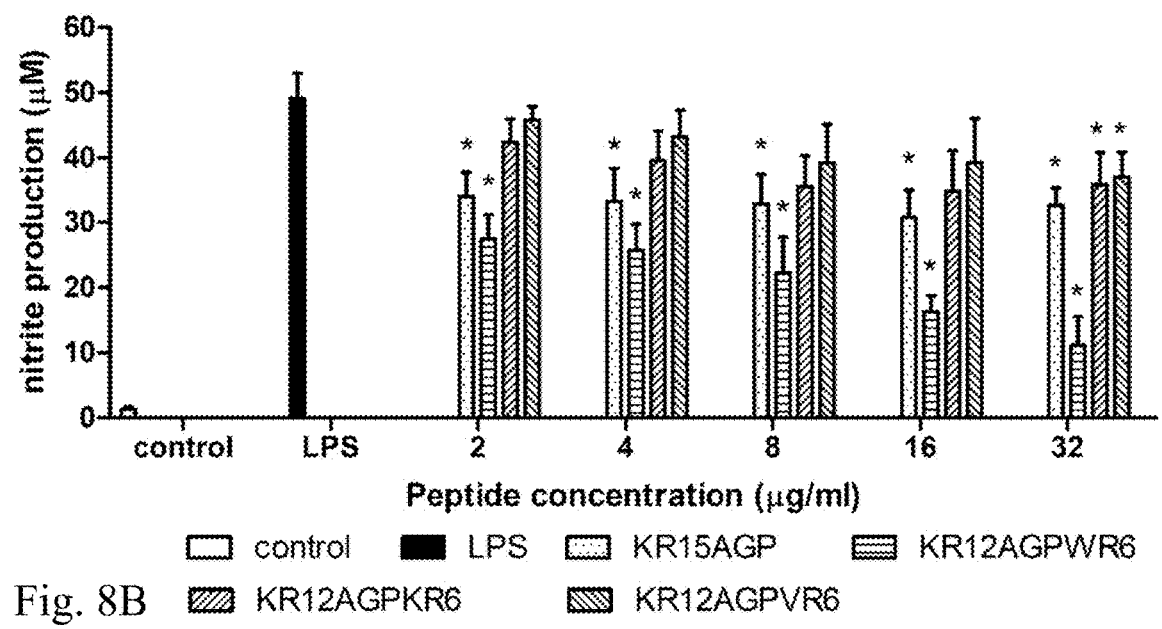
FIGS. 8A-8B illustrate that KR12AGPWR6 inhibit NO (FIG. 8A) and TNF-α (FIG. 8B) production.
Figure 8B:
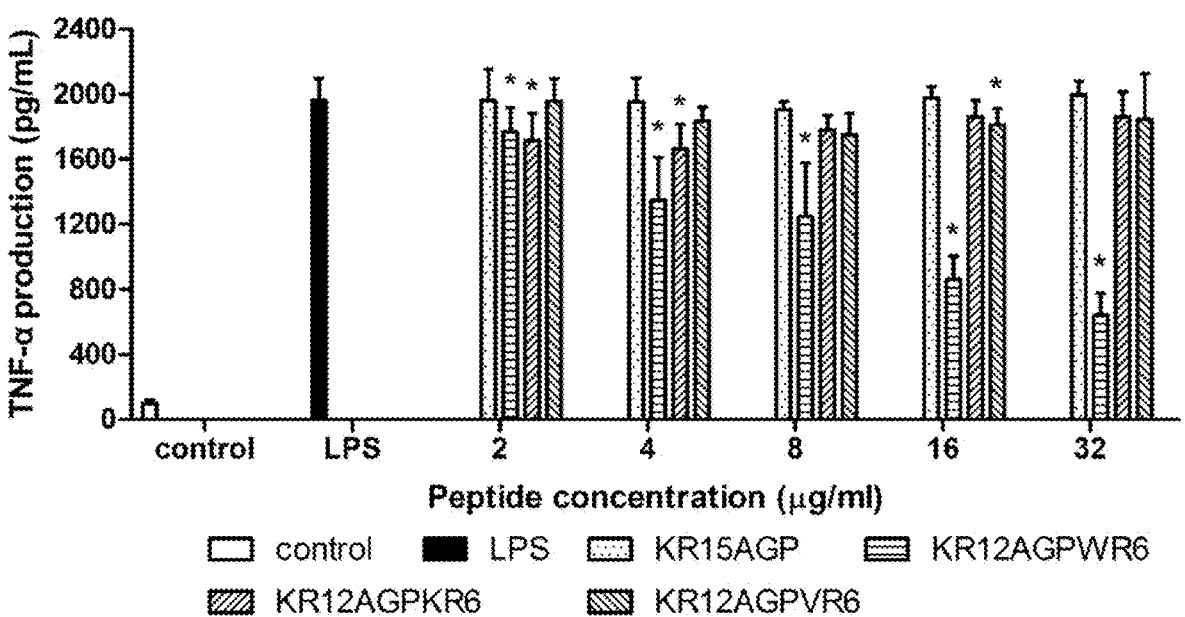

Referring to FIG. 8, only KR12AGPWR6 had the activity to inhibit concentration-dependently NO production (FIG. 8A). Similarly, KR12AGPWR6 also inhibited TNF-α release (FIG. 8B).

Example 9

Mouse Model of Endotoxemia 5-week old male C57BL/6 mice were purchased from National Laboratory Animal Center (Taiwan). Mice were divided into three groups (five in each group) with intraperitoneal (i.p.) injection of (a) 18 mg/kg of body weight *E. coli* O26:B6 LPS, (b) 18 mg/kg body weight LPS plus 10 mg/kg peptide, and (c) no treatment. Blood was collected via tail vein 1.5 hours after injection. Whole blood was centrifuged at 3,000 rpm at 4° C. for 10 minutes. After 24 hours, all mice were sacrificed. The lungs were removed and fixed in 4% formaldehyde buffer, and deparaffinized in UltraClear buffer (J. K. Baker) and graded ethanol. Histology of lung sections was performed by hematoxylin and eosin (H&E) staining. Tissue images were captured using light microscope (Eclipse E400, Nikon) with digital microscopy camera (AxioCam ICc 5, ZEISS).

Figure 9A:
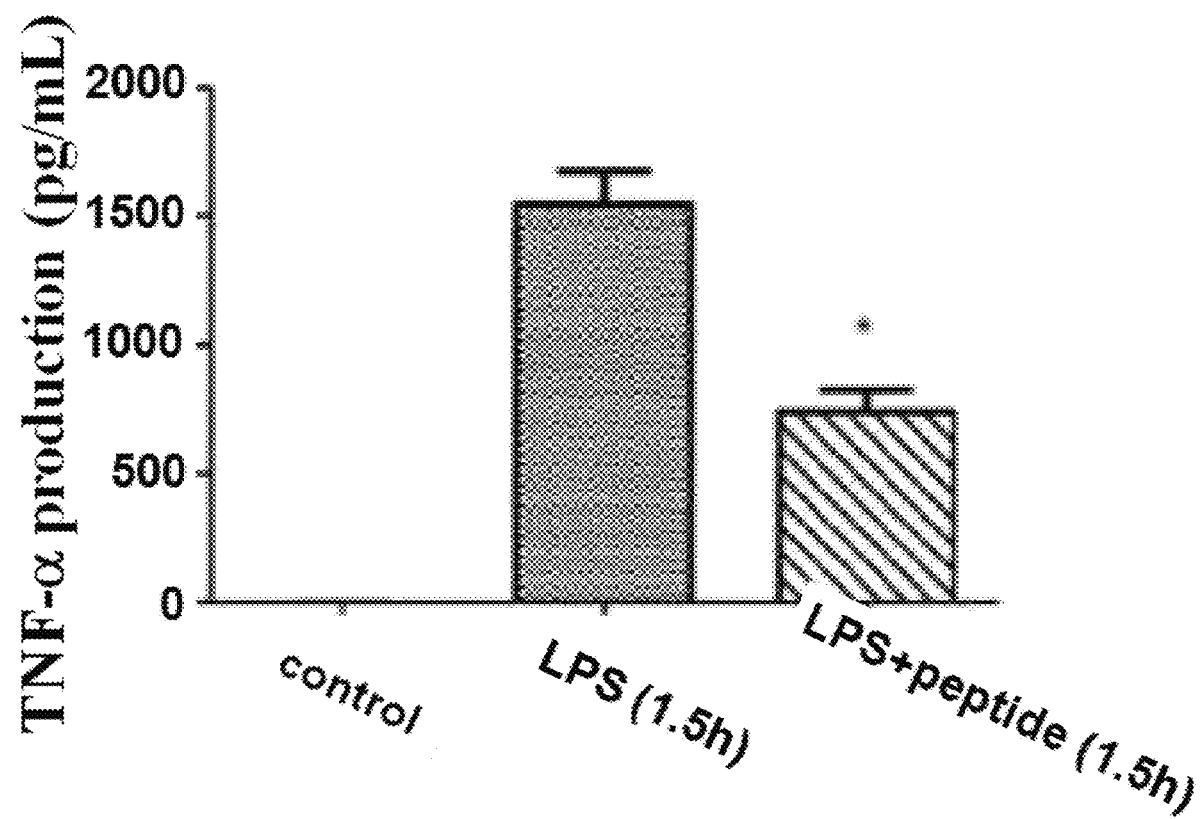
FIGS. 9A-9B illustrate that KR12AGPWR6 suppress the level of TNF-α (FIG. 9A) and improve the proliferation of alveolar epithelial cells and pulmonary hemorrhage (FIGS. 9B-9D) in mice.
Figure 9B:
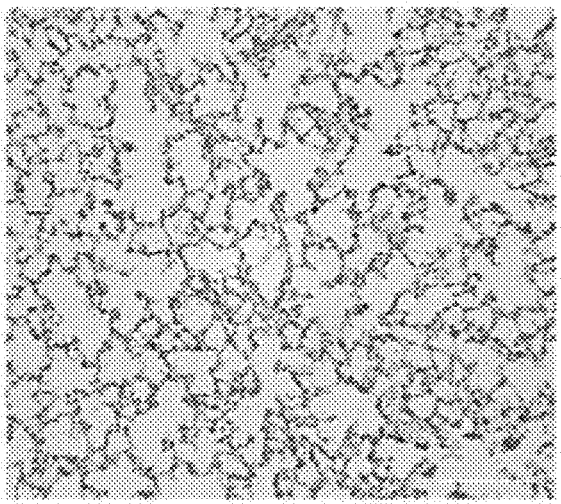
Figure 9C:
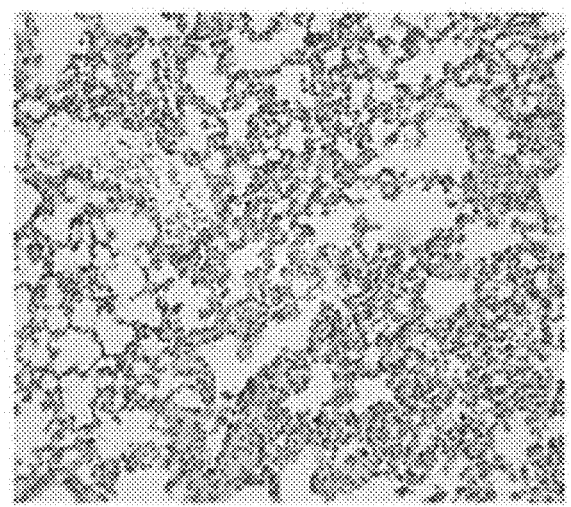
Figure 9D:
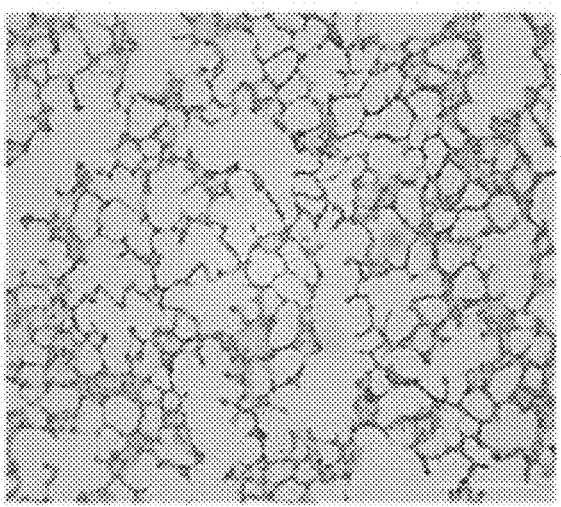

Referring to FIG. 9, KR12AGPWR6-treated mice displayed the significantly lower level of TNF-α (FIG. 9A). KR12AGPWR6 significantly decreased the proliferation of alveolar epithelial cells and pulmonary hemorrhage (FIGS. 9B, 9C, and 9D).

The present invention provides an anti-endotoxin polypeptide having the formula (I) $A_1$-L-$C_1$, wherein one terminus of the peptide is amphipathic and another terminus is hydrophobic. A bent hinge is located between the two terminuses as "L" of formula (I) to produce the helical turn structures, and therefore, the anti-endotoxin activity of the peptide of the invention can be regulated. As mentioned above, for example, when "L" is AGP, the anti-endotoxin peptides not only have anti-endotoxin activity, but also have anti-bacteria and anti-inflammation activities. Actually, the present invention is not limited to AGP, "L" of formula (I) may be selected from G(Gly), P(Pro), or GP(Gly-Pro). Similar to AGP, all these peptides also have the activities of anti-endotoxin and anti-bacteria, and significantly decrease inflammation, such as the angeiorrhagia due to increased vascular permeability caused by inflammation. Since the test results of G(Gly), P(Pro), or GP(Gly-Pro) are similar to that of AGP, it is not necessary to go into details here.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. An anti-endotoxin polypeptide having formula (I)

$$A_1\text{-}L\text{-}C_1 \quad (I)$$

wherein $A_1$ and $C_1$ independently are a short peptide with an α-helix structure in the termini of the formula (I), wherein if $A_1$ is an amphipathic short peptide then $C_1$ is a hydrophobic short peptide, if $A_1$ is the hydrophobic short peptide then $C_1$ is the amphipathic short peptide, wherein the hydrophobicity of the hydrophobic terminus in the formula (I) is between about 0.425 and 0.765, wherein $A_1$ and $C_1$ independently are a short peptide of 6-12 amino acids, wherein $A_1$ is selected from the group consisting of KRIVQR (SEQ ID NO:7) and KRIVQRIKDFLR (SEQ ID NO:8), wherein $C_1$ is selected from the group consisting of IKDFLR (SEQ ID NO:9), RRWWRW_(SEQ ID NO:10), and RRLVRI_(SEQ ID NO:11), L is an amino acid or oligopeptide of 2-3 amino acids, and wherein L is selected from the group consisting of G (Gly), P (Pro), GP (Gly-Pro), and AGP (Ala-Gly-Pro), and wherein the formula (I) polypeptide is selected from the group consisting of KRIVQRAGPIKDFLR (SEQ ID NO: 3), KRIVQRIKDFLRAGPIKDFLR (SEQ ID NO: 4), KRIVQRIKDFLRAGPRRWWRW (SEQ ID NO: 5), and KRIVQRIKDFLRAGPRRLVRI (SEQ ID NO: 6).

2. The anti-endotoxin polypeptide of claim 1, wherein the anti-endotoxin polypeptide is linked to a lipopolysaccharide (LPS).

3. A pharmaceutical composition comprising the anti-endotoxin polypeptide of claim 1 and a pharmaceutically acceptable carrier.

* * * * *